United States Patent
Kale et al.

(10) Patent No.: US 7,371,575 B2
(45) Date of Patent: May 13, 2008

(54) PROCESS FOR EX VIVO FORMATION OF MAMMALIAN BONE AND USES THEREOF

(75) Inventors: Sujata Kale, Boston, MA (US); Michael W. Long, Northville, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 506 days.

(21) Appl. No.: 10/862,972

(22) Filed: Jun. 8, 2004

(65) Prior Publication Data

US 2004/0225374 A1 Nov. 11, 2004

Related U.S. Application Data

(62) Division of application No. 09/753,043, filed on Dec. 27, 2000, now Pat. No. 6,811,776.

(60) Provisional application No. 60/173,350, filed on Dec. 28, 1999.

(51) Int. Cl.
*C12N 5/08* (2006.01)

(52) U.S. Cl. .................... 435/372; 435/4; 435/29; 435/366; 435/384; 424/93.7

(58) Field of Classification Search .................... None
See application file for complete search history.

(56) References Cited

U.S. PATENT DOCUMENTS

| | | | |
|---|---|---|---|
| 4,443,546 A | 4/1984 | Stemerman et al. | 435/240 |
| 4,533,637 A | 8/1985 | Yamane et al. | 435/240 |
| 5,063,157 A | 11/1991 | Stockinger | 435/240.2 |
| 5,405,772 A | 4/1995 | Ponting | 435/240.31 |
| 5,643,736 A | 7/1997 | Bruder et al. | 435/4.21 |
| 6,152,964 A | 11/2000 | Van Blitterswijk | 623/23.72 |

FOREIGN PATENT DOCUMENTS

| | | |
|---|---|---|
| EP | 481791 | 4/1992 |
| EP | 0798374 | 10/1997 |
| WO | WO 95/06112 | 3/1995 |
| WO | WO 96/05290 | 2/1996 |

(Continued)

OTHER PUBLICATIONS

Aubin et al., "Isolation of bone cell clones with differences in growth, hormone responses, and extracellular matrix production," *J. of Cell Biol.* 92:452-461, 1982.

(Continued)

*Primary Examiner*—Leon B. Lankford, Jr.
*Assistant Examiner*—Allison M. Ford
(74) *Attorney, Agent, or Firm*—Fulbright & Jaworski, LLP

(57) ABSTRACT

The present invention concerns methods for the ex vivo formation of mammalian bone and subsequent uses of the bone. A critical and distinguishing feature of the present invention are defined tissue culture conditions and factors resulting in the formation of bone cell spheroids. The invention also provides for methods of implanting into subjects the ex vivo formed bone. Also described are methods for genetically altering the bone cell spheroids to affect bone formation, identification of candidate modulators of bone formation, and identification of genes involved in bone formation.

5 Claims, 10 Drawing Sheets

FOREIGN PATENT DOCUMENTS

| WO | WO 00/06150 | 2/2000 |
|---|---|---|
| WO | WO 00/66178 | 11/2000 |

OTHER PUBLICATIONS

Denker et al., "Formation of cartilage-like spheroids by micromass cultures of murine C3H10T1/2 cells upon treatment with transforming growth factor-beta 1," *Differentiation* 59:25-34, 1995.

Hall and Miyake, "Divide, accumulate, differentiate: cell condensation in skeletal development revisited," *International Journal of Developmental Biology* 39:881-893, 1995.

Harris et al., "Effects of transforming growth factor beta on bone nodule formation and expression of bone morphgenetic protein 2, osteocalcin, osteopontin, alkaline phosphatase, and type I collagen mRNA in long-term cultures of fetal rat calvarial osteoblasts," *J. Bone Min. Res.*, 9(6):855-863, 1994.

Jayme, "Nutrient optimization for high density biological production applications," *Cytotechnology* 5(1):15-30, 1991.

Kale et al., "Three-dimensional cellular development is essential for ex vivo formation of human bone," *Nat. Biotechnol.*, 18:954-958, 2000.

Lawson et al., "Isolation and preliminary characterization of a monoclonal antibody that interacts preferentially with the liver isoenzyme of human alkaline phosphatase," *Clin Chem*, 31:381-385, 1985.

Long, "Expression of human bone-related proteins in the hematopoietic microenvironment," *J Clin. Invest.*, 86:1387-1395, 1990.

Long, "Regulation of human bone marrow-derived osteoprogenitor cells by osteogenic growth factors," *J. Clin. Invest.*, 95:881-887, 1995.

Malaval et al., "Cellular expression of bone-related proteins during in vitro osteogenesis in rat bone marrow stromal cell cultures," *J. Cell. Phys.*, 158:555-572, 1994.

Miyake et al., "Stage-specific onset of condensation and matrix deposition for Meckel's and other first arch cartilages in inbred C57BL/6 mice," *Journal of Craniofacial Genetics & Developmental Biology*, 16:32-47, 1996.

Oberlender and Tuan, "Spatiotemporal profile of N-cadherin expression in the developing limb mesenchyme," *Cell Adhesion & Communication*, 2:521-537, 1994.

Shull et al., "Identification of a vitamin D responsive protein on the surface of human osteosarcoma cells," *Proc. Nat'l Acad. Sci. USA*, 86:5405-5410, 1989.

Siggelkow et al., "Proliferation and Differentiation of human osteoblast—like cell in culture—an in-vivo model of osteoblast development," *J. of Bone and Mineral Res.*, 8(S1):S300, 1993.

Turksen et al., "Isolation of monoclonal antibodies recognizing rat bone-associated molecules in vitro and in vivo," *J Histochem Cytochem*, 40:1339-1352, 1992.

Wong and Tuan, "Interactive cellular modulation of chondrogenic differentiation in vitro by subpopulations of chick embryonic calvarial cells," *Developmental Biology* (Orlando), 167:130-147, 1995.

Woodward and Tuan, "N-Cadherin expression and signaling in limb mesenchymal chondrogenesis: stimulation by poly-L-lysine," *Developmental Genetics*, 24:178-187, 1999.

Yoo et al., "The chondrogenic potential of bone-marrow-derived mesenchymal progenitor cells," *J. Bone Join Surg.*, 80A(12):1745-1757, 1998.

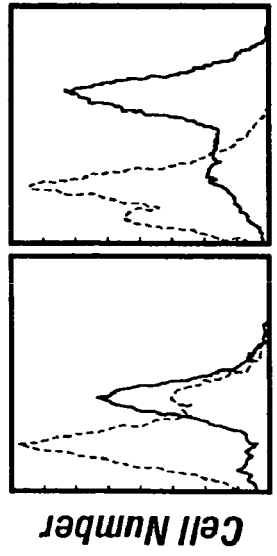
FIG. 8A  α2-Integrin MG63
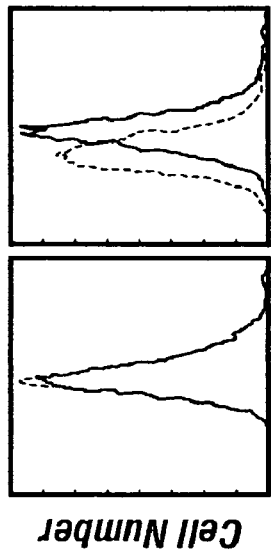
FIG. 8B  α3-Integrin HBPCs
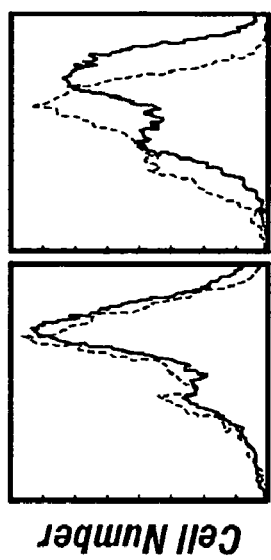
FIG. 8C  α2-Integrin Osteoblasts
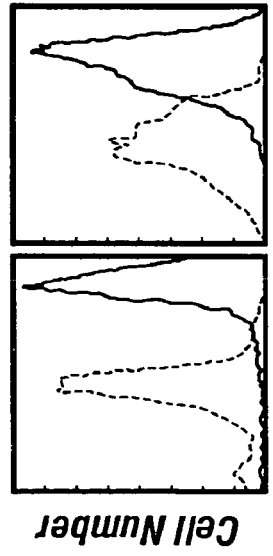
FIG. 8D  β1-Integrin MG63
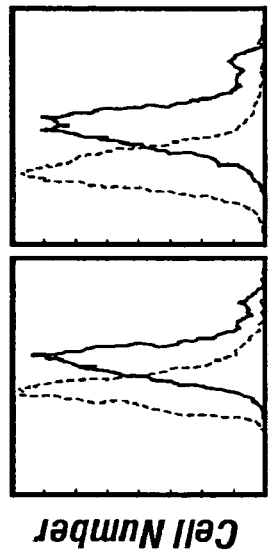
FIG. 8E  β1-Integrin HBPCs
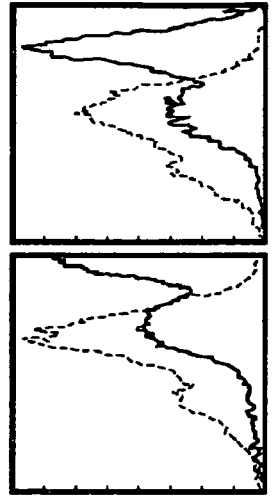
FIG. 8F  β1-Integrin Osteoblasts

PROCESS FOR EX VIVO FORMATION OF MAMMALIAN BONE AND USES THEREOF

This is a divisional of application Ser. No. 09/753,043 filed Dec. 27, 2000, now U.S. Pat No. 6,811,776 which claims priority to U.S. Provisional Application Ser. No. 60/173,350, filed Dec. 28, 1999. The entire content of the foregoing application is hereby incorporated by reference.

The government owns rights in the present invention pursuant to grant number HL59495 and AG43460 from the National Institutes of Health.

BACKGROUND OF THE INVENTION

1. Field of the Invention

The present invention relates generally to the fields of biology and medicine. More particularly, it concerns a process for the ex vivo formation of bone and uses thereof.

2. Description of Related Art

The development of a functional tissue such as bone requires the concerted action of a number of microenvironmental signals: cytokines/growth factors, extracellular matrix (ECM) molecules, and cell:cell interactions. Moreover, these regulatory signals must be queued in the appropriate temporal and spatial order, resulting in a developmental microenvironment that facilitates three-dimensional growth. The skeletal system is no exception to such requirements. It is well understood that a number of cytokines/growth factors, such as TGF-β1 family members, modulate bone formation, and that ECM molecules like osteonectin, osteocalcin, and Type I and II collagen, etc., are important in both osteogenesis and chondrogenesis. As opposed to in vitro systems that are predominately planar, the need for three-dimensional tissue-like development is implicit both in the structural nature of the skeleton and its embryonic development. However, the extension of these in vivo spatial requirements to in vitro systems has been difficult and largely overlooked.

Cellular condensation, a process of cell aggregation mediated by mesenchymal:epithelial cell interactions, plays a crucial role during skeletogenesis (Hall and Miyake, 1992; 1995; Stringa et al., 1997). In the developing chick embryo, cellular condensation precedes differentiation into to prechondrocytes (Hall and Miyake, 1995). In contrast, during osteogenesis, cells differentiate to preosteoblasts and then undergo condensation (Hall and Miyake, 1995; Centrella, 1987). This condensation nonetheless precedes osteoblast differentiation and matrix mineralization (Dunlop and Hall, 1995). Studies of prechondrocytes demonstrate that cell condensation is cytokine-mediated, and induces changes in the expression of a number of developmentally important genes. For example, TGF-β1 or BMP2 both stimulate chondrocytic condensation and up-regulate fibronectin, N-CAM, and tenascin (Hall and Miyake, 1995). The requisite step of cellular condensation during mesenchymal chondrogenesis is mimicked in vitro in chondrocyte micromass cultures (Denker et al., 1995). Tuan and colleagues have demonstrated that TGF-β1 treatment of the multipotent C3H10T1/2 cells in small volumes of media at high cell density (i.e., micro-mass cultures) results in the formation of three dimensional structures that are cartilaginous in nature (Denker et al., 1995). These cellular condensations are associated with the up-regulation of cartilage extracellular matrix components such as Type II collagen and cartilage link protein (Denker et al., 1995). Likewise, studies of embryonic chick (calverial or limb-bud) cells confirm the cell-density mediated induction of chondrogenesis (Wong and Tuan, 1995; Woodward and Tuan, 1999), and demonstrate an obligate requirement for cell:cell interaction in this process, most likely mediated by N-cadherin (Woodward and Tuan, 1999), or N-CAM (Oberlender and Tuan, 1994; Miyake et al., 1996).

To date, no in vitro models of tissue-like osteogenic cell growth or cellular-condensation exist. Calverial or bone marrow-derived osteogenic cells are typically grown on two-dimensional (i.e., planar) surfaces. Cell proliferation eventually leads to a localized piling of confluent cells into "bone nodules." This suggests that cell-density plays a role in the process of bone formation; however, studies directly demonstrating a relationship between cell-density and bone-formation are lacking, as are studies demonstrating the formation of three dimensional, crystalline bone (as opposed to reports concerning the mineralization of the extracellular matrix surrounding bone).

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's own tissue is that the graft will not evoke an immune response. However, using an autograft requires a second surgical site, which increases the risk of infection and may introduce additional complications. Further, bone available for grafting comes from a limited number of sites, for example, the fibula, ribs and iliac crest. An allograft is tissue taken from a different organism of the same species, and a xenograft from an organism of a different species. The latter types of tissue are readily available in larger quantities than autografts, but genetic differences between the donor and recipient may lead to rejection of the graft. All have advantages and disadvantages, yet none provides a perfect replacement for the missing bone.

There exists a need for a better way to repair and/or replace bone in subjects suffering from bone diseases or bone traumas.

SUMMARY OF THE INVENTION

The present invention concerns methods for the ex vivo formation of mammalian bone and subsequent uses of that bone. A critical and distinguishing feature of the present invention are defined tissue culture conditions and factors resulting in the formation of bone cell spheroids. "Bone cell spheroids" are defined as a tissue-like three dimensional growth of osteogenic cells or osteogenic precursor cells. The formation of bone cell spheroids permits the formation of bone within the spheroid. The invention also provides for methods of implanting the ex vivo formed bone into subjects. Also described are methods for genetically altering bone cells/spheroids to affect bone formation, identification of candidate modulators of bone formation, and identification of genes involved in bone formation.

Specifically, the present invention concerns a method for producing mammalian bone ex vivo by obtaining an osteogenic or bone precursor cell; culturing the cell under serum free conditions in the presence of one or more osteogenic growth factors; and establishing the cell cultures at cell densities that allow the formation of a bone cell spheroid containing bone, whereby bone is formed within cells of the bone cell spheroid. The osteogenic or bone precursor cell of the present invention can be isolated from primary sources such as bone marrow or bone explants. Protocols for isolating such cells are described herein. In other embodiments, cell lines of bone cell derivation can be utilized. Osteogenic or bone precursor cells can be from several mammalian species, including but not limited to, human, bovine, equine, canine, feline, chick, rat, or murine origin.

The present invention describes the culturing of the osteogenic cell in defined, serum-free media. Defined medias are described herein as well as additives that are commonly found in these defined medias, including albumin, insulin, an iron source, a fatty acid source and other essential components. The defined serum free media of the present invention also is supplemented with growth factors that are important for the formation of bone cell spheroids. The primary growth factors are broadly defined as members of the Transforming Growth Factor β (TGF-β) gene superfamily. Members of this family include TGF-β1, TGF-β2, TGF-β1.2, and Bone Morphogenic Protein 2 (BMP-2), BMP-4 and BMP-7. Other growth factors such as parathyroid hormone (PTH), calcitonin, 1,25-dihydroxy vitamin D3, interleukin-6, insulin-like growth factors (IGFs) I and II, VEGF and interleukin-11 can be used as solitary or costimulatory factors.

The osteogenic or bone precursor cell of the present invention may be purified by physico-chemical separation techniques, such as equilibrium density separation. In other embodiments, the osteogenic or bone precursor cell may be purified by immuno-affinity isolation, such as those utilizing immune adhesion, immuno-column chromatography, or fluorescence-activated cell sorting. In preferred embodiments, the immuno-affinity isolation utilizes antibodies to osteocalcin, osteonectin, or alkaline phosphatase, or combinations thereof.

The osteogenic or bone precursor cell cultures of the present invention are initiated at cell-densities are from about $1.0 \times 10^3$ to about $1 \times 10^6$ cells per cm$^2$.

Further embodiments of the invention describe a method of providing bone tissue to a mammal, comprising obtaining a bone cell spheroid and implanting the bone cell spheroid into a mammal. The bone cell spheroid may be implanted in a gel, including alginate gels, collagen gels, or fibrin gels. In other embodiments, the bone cell spheroid is implanted in polylactic acid, polyglycolic acid, or PGLA. The bone cell spheroid may also be implanted in or on hydroxyapatitic or other apatitic compounds, devitalized animal bone, devitalized human bone, or porous ceramic structures.

The present invention also concerns implanting a bone cell spheroid in conjunction with orthopedic surgery and/or orthopedic devices, such as hip implants, knee implants, and spinal fusions. Alternatively, implanting a bone cell spheroid is in conjunction with oral surgery and/or dental implants, plastic surgery, or periodontal repairs. Implantation of a bone cell spheroid may be into bone-forming tissue or into a wound. Implantation of a bone cell spheroid also may be into a mammal which has a bone disease such as osteoporosis, Vitamin D deficiency, Osteotitis deformans, Von Recklinghausen's Disease.

The present invention also concerns a method for producing mammalian bone ex vivo by obtaining an osteogenic or bone precursor cell; culturing the cell under serum free conditions in the presence of one or more growth factors of the TGF-β gene superfamily; maintaining the cell cultures at cell densities that allow the formation of a bone cell spheroid, and bone therein; and removing the cellular elements allowing the use of the resulting bone in vivo.

Other embodiments of the invention concern a method for producing mammalian bone ex vivo by obtaining an osteogenic or bone precursor cell; culturing the cell under serum free conditions in the presence of one or more osteogenic growth factors; contacting said cell with a recombinant cDNA containing vector that directs the expression of a protein that enhances bone and/or bone cell spheroid formation; and maintaining the cell cultures at cell densities that allow the formation of a bone cell spheroid. The vector can be a plasmid or a viral vector. Methods for producing and delivering the vector to the osteogenic or bone precursor cell are described. Proteins that enhance bone cell spheroid formation that can be expressed by the cDNA's include, but are not limited to, members of the TGF-β gene superfamily, including TGF-β1, TGF-β2, TGF-β1.2, BMP-2, BMP-4 and BMP-7, as well as cDNA's encoding extracellular matrix proteins such as osteonectin, osteopontin, osteocalcin, bone sialoprotein, collagen, fibronectin, thrombospondin, insulin-like growth factors I or II, or VEGF. Also contemplated are cDNA's directing the expression of cytoadhesion molecules such as integrins, selectins and cadherins, or growth factors such as PTH, calcitonin, interleukin-6 or interleukin-11.

Further embodiments of the invention describe a method for using mammalian bone for bone repair in a subject by obtaining an osteogenic or bone precursor cell; culturing the cell under serum free conditions in the presence of one or more osteogenic growth factors; contacting said cell with a recombinant cDNA containing vector that directs the expression of a protein that enhances bone cell spheroid formation; and initiating the cell cultures at cell densities that allow the formation of a bone cell spheroid; removing the cellular elements from the ex vivo formed bone; and using the formed bone to effect repair.

Another embodiment of the present invention concerns a method for identifying a gene involved in mammalian bone formation, bone repair and/or bone disease by obtaining an osteogenic or bone precursor cell; culturing the cell under serum free conditions in the presence of one or more osteogenic growth factors; initiating the cell cultures at cell-densities that allow the formation of a bone cell spheroid; and identifying genes that are expressed during or following the formation of a bone cell spheroid and not expressed in osteogenic or bone precursor cells cultured in control culture conditions. Methods for identifying genes include differential message display assays, polymerase chain reaction based assays, Northern analysis and gene expression arrays (e.g., cDNA-based or oligonuleotide-based gene chips).

The present invention also concerns a method for producing a modulator of mammalian bone formation, bone repair and/or bone disease by the steps of obtaining an osteogenic or bone precursor cell; culturing the cell under serum free conditions in the presence of a candidate modulator, but in the absence of other osteogenic growth factors; measuring bone cell spheroid formation; and comparing the formation of bone and/or bone cell spheroid with that observed in the presence of one or more osteogenic growth factors. In another embodiment, the present invention concerns a method for identifying a modulator of mammalian bone formation, bone repair or bone disease by obtaining an osteogenic or bone precursor cell; culturing said cell under serum free conditions in the presence of a candidate modulator plus the presence of one or more growth factors of the TGF-β gene superfamily; measuring bone cell spheroid formation; comparing the formation of bone cell spheroid with that observed in the absence of the modulator, and producing a modulator so identified. Modulators identified by this assay would be expected to enhance, inhibit, or act synergistically with growth factors of the TGF-β gene superfamily. Currently, the best example of this latter concept is shown by co-stimulation of spheroid formation with TGFB1 and PTH which increases the size of the resulting microspicules.

The present invention also describes a bone cell spheroid made by the process of obtaining an osteogenic cell or bone precursor cell; culturing said cell under serum free conditions in the presence of one or more osteogenic growth factors; and maintaining the cell cultures at cell densities that allow the formation of a bone cell spheroid.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A. Cell lysates were analyzed by Western analysis for osteonectin and alkaline phosphatase. Type I collagen synthesis was determined by labeling spheroids with $^3$H-Proline and α1 (I) and α1 (III) Collagen chains distinguished by delayed reduction electrophoresis. FIG. 5B. Enzymatic Alkaline Phosphatase Activity. Cells were cultured as in A and enzymatic activity determined colorimetrically. The results are expressed as μmol para-nitrophenol/hr/mg protein. Values are mean±SD (n=4)

FIG. 6A. Bone cell spheroids were formed at the cell densities indicated. (MG63 and Osteoblasts were plated at 1, 2, 4×10$^5$ cells/well, the HBPCs at 1,2,4×10$^6$ cells per well). Osteonectin expression was determined by Western analysis. FIG. 6B. Bone protein expression increases with increasing spheroid size. Spheroids were separated into small, medium, and large size population based on their size (approximately 3,000, 30,000, and 100,000 cells/spheroid, respectively).

FIG. 7A. Bone cell spheroid formation was examined at the time points indicated. Osteonectin and alkaline phosphatase expression was determined by Western analysis. FIG. 7B. Relative protein abundance, expressed in Arbitrary O.D. units, was normalized for protein load, determined by densitometry (MG63 and HBPC). For primary osteoblasts, enzymatic alkaline phosphatase was determined as described in the Methods.

FIG. 8. Bone Cell Spheroid Formation Induces α-Integrin Chain Expression. Bone cell-spheroid formation was induced as described in Methods, and evaluated for integrin expression (bold histograms) by flow cytometry after disaggregation using collagenase/trypsin treatment. Controls (light histograms) consisted of adherent bone cells grown as a two-dimensional planar sheet. No changes in integrin expression is seen in control cells in the presence or absence of TGF-β1.

DESCRIPTION OF ILLUSTRATIVE EMBODIMENTS

Figure 1:
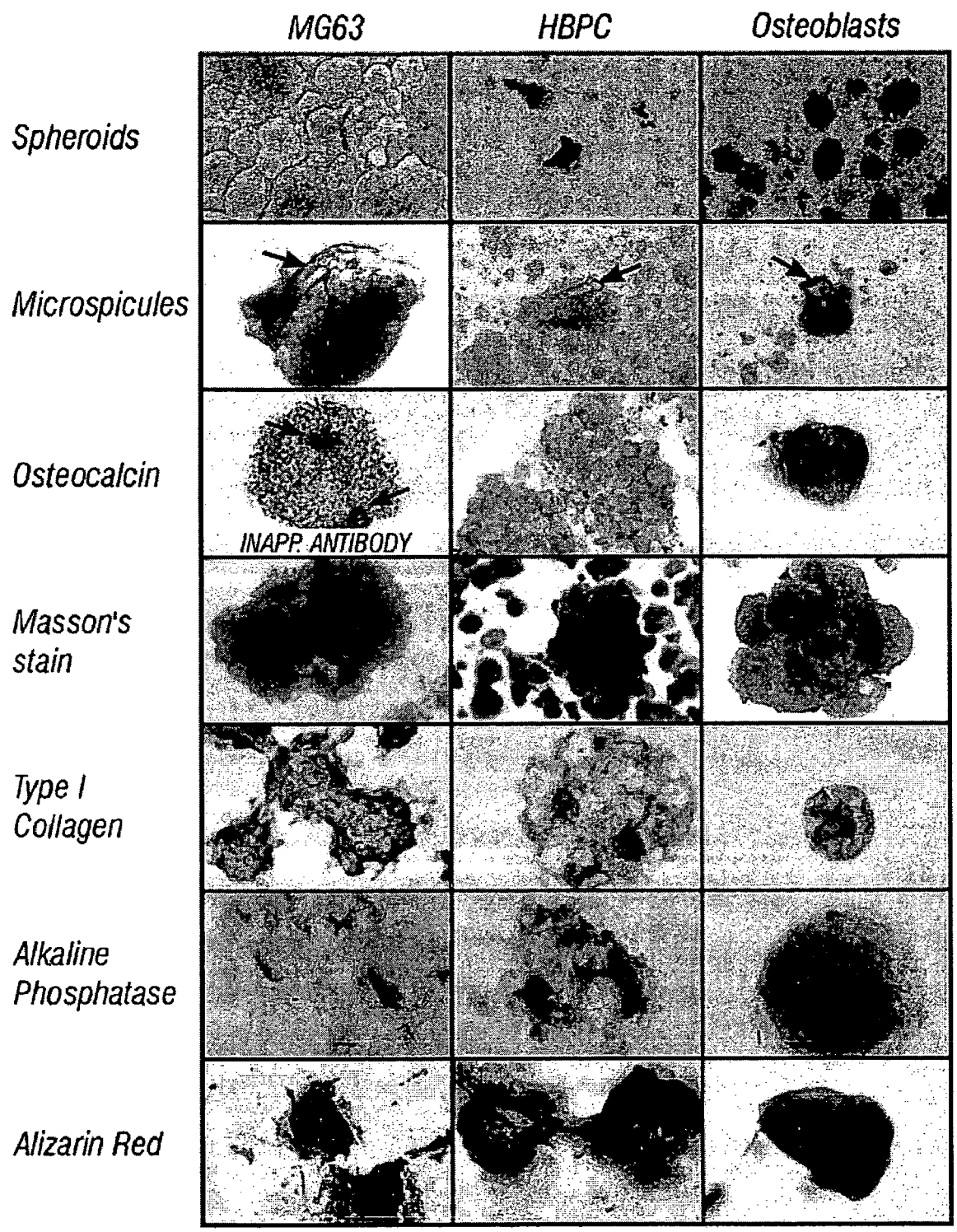
FIG. 1. Cell Spheroid and Microspicule Formation and the Immunocytochemical Analysis. Cells cultured in presence of TGF-β1 (200 pM) formed spheroids (Row 1) and crystalline bone structures termed microspicules (Row 2). Bone cell spheroids express osteonectin (Row 3), and collagen (Masson's stain, Row 4). Type I collagen was also determined by immunocytochemical analysis. (Row 5). Bone cell spheroids also show alkaline phosphatase activity (Row 6) and undergo mineralization as determined by positive Alizarin Red Cytochemistry (Row 7). MG63, a human osteosarcoma cell line; HBPC, human bone precursor cells; osteoblasts, primary human osteoblasts from collagenase treated bone chips.

The rate of bone fractures in the United States is estimated at 6,000,000 individuals per year. When a bone is completely fractured, a significant number of fractures require medical intervention beyond simple immobilization (casting), particularly those involving trauma. A major problem in such instances is the lack of proximity of the two bone ends (referred to as non-union). This results in an inappropriate and prolonged repair process, which may prevent recovery. The average length of time for the body to repair a fracture is 25-100 days, for moderate load-bearing, and one year for complete repair. Thus, both simple fractures and medically complicated breaks would benefit from novel therapeutic modalities which accelerate and/or complete the repair process. The same is true for those bone diseases (referred to as osteopenias) which result in a thinning of the bone the primary symptom of which is an often-debilitating fracture, and other diseases in which bone strength or elasticity is compromised.

There is no curative treatment for lost bone mass, including various growth-promoting proteins and Vitamin D3. Likewise, there is no effective replacement or implant for non-union fractures or crush injuries of the bone. Currently, these latter types of injury utilize bovine (cow), or human cadaver bone which is chemically treated (to remove proteins) in order to prevent rejection. However, such bone implants, while mechanically important, are biologically dead (they do not contain bone-forming cells, growth factors, or other regulatory proteins). Thus, they do not greatly modulate the repair process.

The present invention concerns methods for the ex vivo formation of mammalian bone and subsequent uses of the bone. A critical and distinguishing feature of the present invention are defined tissue culture conditions and factors resulting in the formation of bone cell spheroids. Sources of osteogenic or bone precursor cells and methods of isolating these precursor cells are also described. The invention also provides for methods of implanting into subjects the ex vivo formed bone for the treatment of various bone diseases or bone fractures, breaks or other traumas. Also described are methods for genetically altering the bone cell spheroids to affect bone formation, identification of candidate modulators of bone formation, and identification of genes involved in bone formation.

I. Bone Cell Spheroids

Under normal culture conditions, osteogenic cells are grown in the presence of varying amounts of serum, and remain adherent to the culture dish, essentially growing as a two dimensional, planar sheet of cells. The in vitro expansion of these cells requires their release from the plastic by trypsin treatment and reculturing. After 4 to 6 weeks, the cells are placed in media containing serum and higher levels of calcium and phosphate. These cells reach confluent densities, and then "pile up" forming multi-layered cell structures referred to as bone nodules that mineralize their surrounding extracellular matrix.

In sharp contrast, osteogenic cells grown in serum-free conditions undergo a distinctly different developmental pattern resulting in the creation of a new composition of matter. This process requires the presence of TGF-β, or other osteogenic growth factors, added within the first 0 to 48 hours of culture. Under these conditions, the cells become plastic adherent for an additional 24 to 36 hour period; spontaneously release from the plastic surface of the tissue culture dish; form non-adherent variably sized three-dimensional spheroid-shaped cell aggregates, termed "bone cell spheroids." The bone cells within the spheroids, due to their tissue-like three dimensional development, undergo cellular differentiation resulting in biochemical changes leading to rapid (3 to 7 day) mineralization of the spheroid, and the formation of crystalline bone-like structures (termed microspicules). The composition of matter described herein (of microspicule-containing cell spheroids) differs distinctly from normal bone cell cultures. First and foremost, this process results in spheroidal, three-dimensional, tissue-like development of bone cells. Second, these tissue-like aggregates are non-adherent, developing in suspension with the cells only adherent to each other and not the underlying culture dish plastic. Lastly, the tissue-like development of bone cells requires serum-free conditions and results in the ex vivo formation of three dimensional crystalline bone within the tissue aggregate, a process not observed or described in any other culture system.

II. Osteogenic Precursor Cells

The present invention describes the ex vivo formation of bone from osteogenic cells, bone precursor cells, as well as bone cell lines. The following section describes various sources of these precursor cells, their isolation and characterization. Osteogenic or precursor cells are derived from primary sources such as bone marrow or bone. In addition, cells can be derived from several different species, including cells of human, bovine, equine, canine, feline and murine origin.

A. Bone Precursor Cells

Human bone precursor cells are characterized as small-sized cells that express low amounts of bone proteins (osteocalcin, osteonectin, and alkaline phosphatase) and have a low degree of internal complexity (Long et al., 1995). When stimulated to differentiate, these preosteoblast-like cells become osteoblast-like in their appearance, size, antigenic expression, and internal structure. Although these cells are normally present at very low frequencies in bone marrow, a process for isolating these cells has been described (Long et al., 1995). U.S. Pat. No. 5,972,703, entitled "Bone Precursor Cells: Compositions and Methods," Michael W. Long and Kenneth G. Mann, further describes methods of isolating and using bone precursor cells, and is specifically incorporated herein by reference.

An example of a technique for isolating bone precursor cells involves the following steps. Mononuclear cells are prepared from bone marrow by separation on ficoll or other suitable equilibrium density separation techniques known to those of skill in the art. Low-density mononuclear cells are then cultured overnight culture to remove plastic-adherent cells. An enrichment step using immuno-affinity isolation involves collection of non-adherent low-density cells using anti-osteonectin (ON) and anti-osteocalcin (OC) antibodies immobilized on plastic as described (Long et al., 1995). The immune adherent cells were collected by trypsinization. Alternative enrichment steps may involve immuno-column chromatography or fluorescence-activated cell sorting. In addition to antibodies to osteonectin and osteocalcin, antibodies to alkaline phosphatase or other cell surface markers expressed on bone precursor cells can be utilized. These are described in greater detail in a following section.

As used herein, a bone precursor cell is any cell that is capable of differentiating or expanding into an osteoblast cell. A bone precursor cell of the present invention is not hematopoietic and thus does not express the pan-hematopoietic antigen CD34. Preferred bone precursor cells include osteoprogenitor cells and preosteoblast cells.

Bone precursor cells can be further enriched by equilibrium-density centrifugation of bone marrow cells. Equilibrium-density centrifugation of bone marrow cells provides low density bone marrow cells enriched in bone precursor cells. In one embodiment, equilibrium-density centrifugation can be performed before the antibody purification. In a second embodiment, equilibrium-density centrifugation can be performed after the antibody purification. Alternatively, the equilibrium-density centrifugation purification step can be performed twice before and after the antibody purification step.

In another aspect, the population of bone precursor cells can be enriched by removing stromal cells present in bone marrow cells. Removal of stromal cells can be accomplished by exposing bone marrow cells to an adherent surface, typically tissue culture plastic or glass. Stromal cells adhere to tissue culture plastic or glass while bone precursor cells do not. Stromal cells can be removed before or after the immune purification step. Preferably, stromal cells are removed prior to the immune purification step. The use of solid surfaces such as tissue culture plastic or glass is well known in the art. Tissue culture plastic and glass can be treated (e.g., silicone, nitrocellulose, nickel, etc.) to promote or inhibit cell adhesion. Treated and untreated surfaces are available commercially.

In another aspect, an enriched population of bone precursor cells is further fractionated according to size. In a preferred embodiment, size fractionation can be accomplished by fluorescence activated flow cytometry. Bone precursor cells of the present invention have average diameters of between about 8 microns and about 70 microns. Preferably, bone precursor cells have average diameters of between about 10 microns and about 20 microns.

B. Primary Human Osteoblasts

Another source of bone cells for use in the present invention are primary osteoblasts. An example of an isolation procedure for these cells can be found in Robey and Termaine (1985). Briefly, bone chips are obtained during orthopedic surgery. These are treated with Collagenase D for 2 hrs at 37° C., the non-adherent cells washed off, the bone pieces minced, and cultured in $Ca^{2+}$—free media containing 10% FCS and Pen/Strep. After the cultures are confluent, the cells are collected by trypsinization and cultured in $Ca^{2+}$-containing DMEM for 2-3 weeks. Bone-derived osteoblasts are recovered by trypsinization.

Alternative methods for isolating osteoblasts from bone are known in the art (see, for example, Aubin et al., 1982). As reported, the calvaria is excised, rinsed in a medium and minced with scissors. The minced bone is digested with collagenase for a short period of time in medium. The cells are removed by centrifugation and decanting the supernatant, leaving the bone pieces behind. Fetal calf serum is added to inhibit the collagenase digestion. Cells are plated at a low density in an appropriate growth medium, and clonal cell colonies are cultured in replicate for continuous culture and characterization.

C. Cell Lines

In addition to primary osteoblasts and bone precursor cells as described above, various cell lines can be used as a starting point for ex vivo bone spheroid formation as described by the methods in the present invention. Cell lines can be from a number of species, including human, bovine, equine, canine, feline and murine origin. Exemplary cell lines as described in the examples included in this invention are MG-63 cells (ATCC #CRL-1427), C3/H10T1/2 cells (ATCC # CCL-226) and SAOS-2 cells (ATCC # HTB-85). Other cell lines, also available through the American Type Culture Collection, include HOS cells (ATCC# CRL-1543) and various derivatives thereof, G-292 (ATCC# CRL-1423), SJSA-1 cells (ATCC# CRL-2098), Hs 3.T cells (ATCC# CRL-7005), TE 415.T cells (ATCC# CRL-7764), TE 418.T cells (ATCC# CRL-7766), Hs 755(A).T cells (ATCC# CRL-7877), 143B cells (ATCC# CRL-8303), U-2 OS cells (ATCC# HTB-96) and T1-73 cells (ATCC# CRL-7943). These cell lines are all derived from human osteosarcomas. Similar osteosarcoma cell lines from several other species are available from ATCC.

III. Cellular Markers

Various cellular markers are used to define and/or purify osteogenic precursor cells of the present invention. The following section defines these markers and their uses.

Bone precursor cells, such as those described in U.S. Pat. No. 5,972,703, herein incorporated in its entirety by reference, are immunoreactive with bone precursor cell antibody. A bone precursor cell antibody is used to enrich the population of bone precursor cells. Bone precursor cell antibodies include anti-osteocalcin, anti-osteonectin, and anti-bone alkaline phosphatase. Anti-osteocalcin, anti-osteonectin, and anti-bone alkaline phosphatase were described in Shull et al., 1984. As bone precursor cells are further characterized, other antibodies which immunoreact with a bone precursor cell may be generated by one of ordinary skill in the art. The use of these other antibodies immunoreactive with a bone precursor cell are contemplated as well. In a preferred embodiment, a bone precursor cell antibody is conjugated to a solid substrate. The solid substrate is preferably a tissue culture or petri dish. The use of solid surfaces such as tissue culture plastic or glass is well known in the art. Tissue culture plastic and glass can be treated (e.g., silicone, nitrocellulose, nickel, etc.) to promote or inhibit protein adhesion. Treated and untreated surfaces are available commercially. Antibody coated tissue culture dishes can be utilized to "pan" for bone precursor cells. Briefly, bone marrow cells containing bone precursor cells are incubated on antibody coated dishes. Bone precursor cells adhere to the antibodies while all other cells do not adhere to the dish. After incubation, the dish non-adherent cells are removed by gently washing the dish with media. Bone precursor cells were removed from the dish and further analyzed, purified or differentiated into osteoblasts.

In another embodiment, a second antibody immunoreactive with a bone precursor cell antibody can be used to enrich the population of bone precursor cells. The use of a secondary antibody is generally known in the art. Typically, secondary antibodies are antibodies immunoreactive with the constant regions of the first antibody. Preferred secondary antibodies include anti-rabbit, anti-mouse, anti-rat, anti-goat, and anti-horse and are available commercially. In a preferred embodiment, secondary antibodies are conjugated to a solid substrate including tissue culture dish, agarose, polyacrylamide, and magnetic particles. In this embodiment, a bone precursor cell antibody is first immunoreacted to a bone precursor cell. The bone precursor cell with the attached antibody is next exposed to the secondary antibody that is conjugated to a solid substrate. Enrichment of precursor cells is achieved because only cells that present a bone precursor cell antibody immunoreact with the secondary antibody. A commercially available kit provides secondary antibodies conjugated to magnetic particles. In this system, bone precursor cells that present a bone precursor cell antibody are purified by exposure to a magnetic field.

The preparation of bone antibodies (i.e., to osteonectin, osteocalcin and alkaline phosphatase) was reported in Shull et al., 1989, incorporated herein by reference. Both polyclonal and monoclonal antibodies are contemplated by the present invention. Means for preparing and characterizing antibodies are well known in the art (See, e.g., E. Harlow and D. Lane, 1988).

Cell surface antigens on normal cells of the osteogenic lineage have been reported for avian and rodent species (Bruder and Caplan, 1989; 1990; Turksen et al., 1992). Some of these antibodies reported also react with cells other than those found in bone. Monoclonal antibodies have been raised against intracellular antigens in normal human osteoblasts and against the surface of transformed human osteogenic cell lines (Embleton et al., 1981; Hosoi et al., 1982; Heiner et al., 1987; Bruland et al., 1988; Tsai et al., 1990; Walsh et al., 1994). Examples of osteogenic cell markers, production of antibodies and hybridomas, as well as methods of using these markers are described in U.S. Pat. No. 5,643,736. An example of a monoclonal antibody against a cell surface epitope capable of identifying human osteogenic cells is one directed against alkaline phosphatase (Lawson et al., 1985). This well-characterized cell surface enzyme has served as the historical standard for identifying a large family of osteogenic cells, and is readily demonstrated by a simple histochemical stain.

Other preferred antigens include osteocalcin and osteonectin. Osteocalcin is a vitamin K-dependent bone calcium binding protein also called bone gla protein (BGP). Particularly, human osteocalcin is a relatively small protein composed of 49 amino acids and having a molecular weight of 5800. This protein is produced from osteoblast, and occupies about 20% of the constituent components of non-collagen protein of the bones. This protein contains gamma-carboxyglutamic acid residues and has a strong affinity for hydroxyapatite, and it is therefore presumed to have an important role in the formation of the bone matrices. Osteonectin, also termed BM40 or SPARC (secreted protein, acidic and rich in cysteine) is a multifunctional glycoprotein involved in tissue mineralization, cell-extracellular matrix interactions as well as angiogenesis. Non-collagenous, calcium-binding glycoprotein of developing bone. It links collagen to mineral in the bone matrix.

The monoclonal antibodies against precursor cells can be labeled with suitable radioactive, enzymatic, fluorescent or other labels by conventional methods and/or bound to suitable solid carriers, which will be apparent to those skilled in the art. For example, monoclonal antibodies can be used in combination with, or coupled to, an immunochemical such as fluorescein isothiocyanate, peroxidase, biotin and its analogs (e.g., iminobiotin), avidin and its analogs (streptavidin), or other such markers. Moreover, monoclonal antibodies can be bound or attached to certain substrates and utilized to capture osteogenic cells when tissue samples such as bone cell isolates, periosteal biopsies, or cultured cells are brought in contact with the attached monoclonal antibodies. The bound cells may then be separated from the solid phase by known methods depending essentially upon the nature of the solid phase and the antibody. The bound cells can be recovered and used for various therapeutic purposes such as for the regeneration of bone, etc., depending upon the various external and internal factors.

As a result, the present invention contemplates any method of employing monoclonal antibodies to separate normal osteogenic cell subsets from other cells such as fibroblastic or hemopoietic cells. For example, a further embodiment of the present invention is directed to a method of producing a population of normal human osteogenic cell subsets comprising the steps of providing a cell suspension of tissue containing such cells; contacting the cell suspension with monoclonal antibodies which recognize an epitope on the osteogenic cells but do not recognize an epitope on the fibroblastic or hemopoietic cells; and separating and recovering from the cell suspension the cells bound by the monoclonal antibodies.

IV. TGF-β Gene Superfamily

The use of growth factors from the TGF-β gene superfamily to produce bone ex vivo is an important aspect of the present invention. The following section details attributes of the TGF-β gene superfamily. Of particular use are growth factors that induce the formation of a bone cell spheroid, as defined in the previous section.

The transforming growth factor-β superfamily is a well-characterized family of proteins involved in cellular proliferation and differentiation of cells into various tissues. Members of the TGF-β superfamily are generally dimeric in structure, comprising two monomeric units which are produced by proteolytic cleavage from a larger precursor protein, of which the processed monomer represents the carboxyl terminal portion. The dimeric TGF-β proteins generally have molecular weights of approximately 20,000 to 35,000 and share a common cysteine pattern in the mature protein region. See, for example, Sporn et al. (1986) and the papers cited therein. The TGF-β superfamily includes several subgroups beside TGF-β1 through -β5. These are the bone morphogenetic proteins (BMPs), growth and differentiation factors (GDFs), the inhibins, as well as GDNF and Mullerian inhibitory substance and other structurally related proteins. The TGF-β superfamily also includes proteins from other species, which have been characterized and are highly conserved compared to the mammalian TGF-βs, including Vg1 (*Xenopus*), (Weeks and Melton, 1987); Dpp, Screw and 60A (*Drosophila*), (Padgett et al., 1987; Doctor et al., 1992); and more recently identified proteins including Univin (sea urchin), Dorsalin-1 (chicken) and Radar (Zebrafish). Other factors which may be effectively used in the composition include synthetic molecules or fragments of a TGF-β superfamily member which are able to bind to a TGF-β receptor molecule.

The transforming growth factor-β (TGF-β) family of proteins consists of a number of related, but functionally distinct, proteins (Barnard, 1990; Roberts and Sporn, 1990). One member of the TGF-β family of proteins, TGF-β1, is a multifunctional cytokine with both growth promoting and inhibiting activities. Recently, TGF-β1 has been found to play a role in modulating repair of vascular injuries such as restenosis lesions (Nikol et al., 1992) and atherosclerotic plaques (Kojima et al., 1991).

Members of the TGF-β family of proteins initiate cell signaling by binding to heteromeric receptor complexes of type I (TβRI) and type II (TβRII) serine/threonine kinase receptors (reviewed by Massague et al., 1994; Miyazono et al., 1994). Activation of this heteromeric receptor complex occurs when TGF-β binds to TβRII, which then recruits and phosphorylates TβRI. Activated TβRI then propagates the signal to downstream targets (Chen and Weinberg, 1995; Wrana et al., 1994).

Until now, three distinct types of TGF-βs designated as TGF-β1, TGF-β2 and TGF-β3 which are functionally closely related and share a high degree of receptor cross-reactivity have been cloned and characterized by sequence analysis. All TGF-βs are synthesized as 390 to 412 amino acid precursors that undergo proteolytic cleavage to produce the monomeric forms, which consist of the C-terminal 112 amino acids. In their mature, biologically active forms, TGF-βs are acid- and heat-stable disulfide-linked homodimers of two polypeptide chains of 112 amino acids each. The complete amino acid sequences of human (Derynck et al., 1985), murine (Derynck et al., 1986) and simian TGF-β1 (Sharples et al., 1987) show remarkable sequence conservation, differing only in a single amino acid residue. Comparison of the amino acid sequence of human TGF-β1, human TGF-β2 (de Martin et al., 1987; Marquardt et al., 1987) and human TGF-β3 (Ten Dijke et al. 1988) has demonstrated that the three proteins exhibit in their mature forms about 70-80% sequence identity. A heterodimeric TGF-β1.2 has been isolated from porcine platelets and consists of one subunit of TGF-β1 disulfide-linked to one subunit of TGF-β2 (Cheifetz et al., 1987).

The search for the molecule or molecules responsible for formation of bone, cartilage, tendon and other tissues present in bone and other tissue extracts has led to the discovery of a novel set of molecules called the Bone Morphogenetic Proteins (BMPs), which are also members of the TGF-β gene family. The structures of several proteins, designated BMP-1 through BMP-15, have previously been elucidated. The unique inductive activities of these proteins, along with their presence in bone, cartilage and/or other vital tissues, suggests that they are important regulators of bone and other tissue repair processes, and may be involved in tissue formation, maintenance and repair. There is a need to identify improved methods and compositions for formation, maintenance and repair of such tissues.

Members of the bone morphogenetic protein family have been shown to be useful for induction of cartilage and bone formation. For example, BMP-2 has been shown to be able to induce the formation of new cartilage and/or bone tissue in vivo in a rat ectopic implant model, see U.S. Pat. No. 5,013,649; in mandibular defects in dogs (Toriumi et al., 1991); in femoral segmental defects in sheep (Gerhart et al., 1991). Other members of the BMP family have also been shown to have osteogenic activity, including BMP-4, -6 and -7 (Wozney, 1993). BMP proteins have also been shown to demonstrate inductive and/or differentiation potentiating activity on a variety of other tissues, including cartilage, tendon, ligament, neural tissue.

Other factors that are useful in accordance with the present invention include the following: BMP-3 (Vukicevic et al., 1989); growth factors, such as basic fibroblast growth factor (bFGF); glucocorticoids, such as dexamethasone (Cheng et al., 1994); and prostaglandins, such as prostaglandin E1 (Chen et al., 1991). Further, ascorbic acid and its analogs, such as ascorbic acid-2-phosphate (Tennenbaum et al., 1982) and glycerol phosphates, such as β-glycerophosphate (Bruder et al., 1991) are effective adjunct factors for advanced differentiation, although alone they do not induce osteogenic differentiation. Other factors include Inhibin A (Chen et al., 1993), chondrogenic stimulatory activity factor (CSA) (Syftestad et al., 1985), collagenous extracellular matrix molecules, including type I collagen, particularly as a gel (Kimura et al., 1984), and vitamin A analogs, such as retinoic acid (Langille et al., 1989).

Also of interest in the present invention are insulin-like growth factors. IGF-I and IGF-II each have a molecular weight of about 7,500 daltons. Each of IGF-I and IGF-II possesses A and B domains that are highly homologous to the corresponding domains of proinsulin. A and B domains are connected to each other by a C domain. A carboxy-terminal extension, the D domain, is present in IGF, but is not found in proinsulin. Both IGF-I and IGF-II are single-chain polypeptides each with 3 disulfide bridges and have a sequence identity of 49% and 47%, respectively, to human insulin A chain and B chain. Like insulin, IGFs stimulate phosphorylation of specific tyrosine residues within the cytoplasmic domain of the receptors to which they bind, as described in WO 93/98826. The designation "insulin-like growth factor" was chosen to express the insulin-like effects and the insulin-like structure of these polypeptides which act as mitogens on a number of cells, as described in EP 128 733. IGF-I is a 70 amino acid peptide, while IGF-II is a 67 amino acid peptide, as described in Rinderknecht (1978a) and (1978b). IGF-I and IGF-II have 62% structural homology to each other. Both have been isolated from human serum.

Insulin-like growth factors are also known under the class name somatomedins, and have been identified in various animal species as polypeptides that act to stimulate growth of cells in a variety of tissues and cell types, particularly during development. Growth promoting effects of somatomedins include enhancement of cell multiplication and stimulation of cartilage proliferation, stimulation of transport of amino acids, stimulation of synthesis of RNA, DNA and protein, and stimulation of incorporation of sulfate into proteoglycan and of proline into collagen. Much mammalian postnatal growth is due to stimulation of cartilage growth by somatomedins and growth in utero may also be somatomedin-dependent.

Yet another important growth factor that can be utilized according to the present invention is vascular endothelial growth factor/vascular permeability factor (VEGF/VPF). This protein is an endothelial cell-specific mitogen which has been shown to be stimulated by hypoxia and required for tumor angiogenesis. Sanger et al. (1986); Kim et al. (1993); Schweiki et al. (1992); Plate et al. (1992). It is a 34-43 kDa (with the predominant species at about 45 kDa) dimeric, disulfide-linked glycoprotein synthesized and secreted by a variety of tumor and normal cells. VEGF appears to play a principle role in many pathological states and processes related to neovascularization V. Serum-Free Media The present invention calls for the use of serum-free media for growth and differentiation of the osteogenic cells into bone cell spheroids. The following section describes attributes and conditions for using serum-free media.

The use of serum-free culture for the manufacture of recombinant biopharmaceuticals from mammalian cells has been thoroughly reviewed (Barnes, 1987; Barnes and Sam, 1980; Broad et al., 1991; Jayme, 1991). The list of the main additives which are used as supplements for serum-free media is summarized by Barnes (1987) and Barnes & Sam (1980). Most commercially available serum-free media contain a carrier protein such as albumin. The presence of carrier protein might be required for protection of the cell viability.

An example of serum free culture medium can be found in U.S. Pat. No. 5,063,157, herein incorporated by reference. The media described is for non-adherent mammalian cells comprises, in addition to the base medium, transferrin, insulin, a peptone, a beta-D-xylopyranose derivative, selenite and a biological polyamine. Another serum free cell growth medium for mammalian cells is disclosed in U.S. Pat. No. 4,443,546. This growth medium, in addition to the basic medium, contains seven ingredients. European patent specification No. 481,791 discloses a culture medium for CHO cells comprising water, an osmolality regulator, a buffer, an energy source, amino acids, an iron source, a growth factor and other optional components. The two media exemplified contain 19 and 17 components, respectively.

Examples of potential additives to serum free media include the following:

A. Albumin

Albumin is preferably supplied in the form of bovine (BSA) or human serum albumin (HSA) in an effective amount for the growth of cells. Albumin provides a source of protein in the media. Albumin is thought to act as a carrier for trace elements and essential fatty acids. Preferably, the albumin used in the present formulations is free of pyrogens and viruses, and when necessary, is approved regulatory agencies for infusion into human patients. The HSA may be deionized using resin beads prior to use. The concentration of human serum albumin is 1-8 mg/ml, preferably 3-5 mg/ml, most preferably 4 mg/ml.

B. Soluble Carrier/Fatty Acid Complex

The albumin mentioned above could be substituted by a soluble carrier/essential fatty acid complex and a soluble carrier cholesterol complex which can effectively deliver the fatty acid and cholesterol to the cells. An example of such a complex is a cyclodextrin/linoleic acid, cholesterol and oleic acid complex. This is advantageous as it would allow for the replacement of the poorly characterized albumin with a well defined molecule. The use of cyclodextrin removes the need for the addition of human/animal serum albumin, thereby eliminating any trace undesired materials which the albumin would introduce into the media. The use of cyclodextrin simplifies the addition of specific lipophilic nutrients to a serum-free culture.

The lipophilic substances which can be complexed with cyclodextrin include unsaturated fatty acids such as linoleic acid, cholesterol and oleic acid. The linoleic acid, cholesterol and oleic acid are present in effective amounts and can be present in equal proportions such that the total amount is 0.001 to 100 ug/ml, preferably 0.1 to 10 ug/ml. The preparation of such complexes is known in the art and is described, for example, in U.S. Pat. No. 4,533,637, the entire contents of which is hereby incorporated by reference.

C. Iron Source

A source of iron in an effective amount and in a form that can be utilized by the cells can be added to the media. The iron can be supplied carrier molecule, in an effective amount. The transferrin may be derived from animal sera or recombinantly synthesized. It is understood that when transferrin is derived from an animal source, it is purified to remove other animal proteins, and thus is usually at least 99% pure. The transferrin concentration is usually between 80 and 500 ug/ml, preferably between 120 and 500 ug/ml, more preferably between 130 and 500 ug/ml, even more preferably between 275 and 400 ug/ml and most preferably 300 ug/ml. An iron salt, preferably a water soluble iron salt, such as iron chloride (e.g., $FeCl_3.6H_2O$) dissolved in an aqueous solution such as an organic acid solution (e.g., citric acid) is used to supply the iron to transferrin. One mole of iron chloride is usually used for every mole of citric acid. The concentration of iron chloride is 0.0008 to 8 ug/ml, preferably 0.08 to 0.8 ug/ml, most preferably 0.08 ug/ml.

D. Insulin Growth Factor

Insulin also may be added to the media of the present invention in an effective amount. The insulin concentration is between 0.25 and 2.5 U/ml, more preferably 0.4-2.1 U/ml, most preferably 0.48 U/ml. In the conversion of Units to mass, 27 U=1 mg. Therefore, incorporating the conversion, the insulin concentration is approximately between 9.26 ug/ml and 92.6 ug/ml, more preferably 14.8 ug/ml-77.8 ug/ml, most preferably 17.7 ug/ml. It is again understood that human insulin is more preferable than animal insulin. Highly purified recombinant insulin is most preferred. An insulin like growth factor such as insulin like growth factor 1 and insulin like growth factor 2 may be used in place of or in addition to insulin in an amount which provides substantially the same result as a corresponding amount of insulin. Thus, the term "insulin growth factor" includes both insulin and insulin like growth factors.

E. Additional Components

The addition of other lipids to the above essential reagents could enhance the proliferative potential of precursor cells. These components, however, are preferably not added unless they are necessary for a particular experiment or to grow a particular type of cell. Optionally, triglycerides and/or phospholipids may be included as additional sources of lipid. A preferable source of lipid contains a mixture of neutral triglycerides of predominantly unsaturated fatty acids such as linoleic, oleic, palmitic, linolenic, and stearic acid. Such a preparation may also contain phosphatidylethanolamine and phosphatidylcholine. Another source of lipid is a human plasma fraction precipitated by ethanol and preferably rendered virus free by pasteurization.

Other ingredients which can optionally be added to the media are cited in the following references: WO 95/06112, U.S. Pat. Nos. 4,533,637, 5,405,772. The entire contents of all of these references are incorporated by reference.

F. Undesired Components

When the media is to be used to grow cells for introduction into a human patient, the media preferably does not contain ingredients such as bovine serum albumin, mammalian serum, and/or any natural proteins of human or mammalian origin (as explained above). It is preferable that recombinant or synthetic proteins, if they are available and of high quality, are used. Most preferably, the amino acid sequences of the recombinant or synthetic proteins are identical to or highly homologous with those of humans. Thus, the most preferable serum-free media formulations herein contain no animal-derived proteins and do not have even a non-detectable presence of animal protein.

In the most ideal system, optional components which are not necessary are preferably not added to the medium. Such optional components are described in the prior art cited above and may be selected from the group consisting of meat extract, peptone, phosphatidylcholine, ethanolamine, anti-oxidants, deoxyribonucleosides, ribonucleosides, soy bean lecithin, corticosteroids, myoinositol, monothioglycerol, and bovine or other animal serum albumin.

VI. Diseases and Conditions Requiring Bone Repair

The following is a brief discussion of four human conditions to exemplify the variety of diseases and disorders that would benefit from the development of new technology to improve bone repair and healing processes. In addition to the following, several other conditions, such as, for example, vitamin D deficiency.

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would be represent a great advance.

A second example which may benefit from new treatment methods is osteogenesis imperfecta (OI). OI encompasses various inherited connective tissue diseases that involve bone and soft connective tissue fragility in humans (Byers & Steiner, 1992; Prockop, 1990). About one child per 5,000-14,000 born is affected with OI and the disease is associated with significant morbidity throughout life. A certain number of deaths also occur, resulting from the high propensity for bone fracture and the deformation of abnormal bone after fracture repair (OI types II-IV; Bonadio & Goldstein, 1993). The relevant issue here is quality of life; clearly, the lives of affected individuals would be improved by the development of new therapies designed to stimulate and strengthen the fracture repair process.

OI type I is a mild disorder characterized by bone fracture without deformity, blue sclerae, normal or near normal stature, and autosomal dominant inheritance (Bonadio &

Goldstein, 1993). Osteopenia is associated with an increased rate of lone bone fracture upon ambulation (the fracture frequency decreases dramatically at puberty and during young adult life, but increases once again in late middle age). Hearing loss, which often begins in the second or third decade, is a feature of this disease in about half the families and can progress despite the general decline in fracture frequency. Dentinogenesis imperfecta is observed in a subset of individuals.

In contrast, OI types II-VI represent a spectrum of more severe disorders associated with a shortened life-span. OI type II, the perinatal lethal form, is characterized by short stature, a soft calvarium, blue sclerae, fragile skin, a small chest, floppy appearing lower extremities (due to external rotation and abduction of the femurs), fragile tendons and ligaments, bone fracture with severe deformity, and death in the perinatal period due to respiratory insufficiency. Radiographic signs of bone weakness include compression of the femurs, bowing of the tibiae, broad and beaded ribs, and calvarial thinning.

OI type III is characterized by short stature, a triangular facies, severe scoliosis, and bone fracture with moderate deformity. Scoliosis can lead to emphysema and a shortened life-span due to respiratory insufficiency. OI type IV is characterized by normal sclerae, bone fracture with mild to moderate deformity, tooth defects, and a natural history that essentially is intermediate between OI type II and OI type I.

More than 150 OI mutations have been characterized since 1989 (reviewed in Byers & Steiner, 1992; Prockop, 1990). The vast majority occur in the CO1A1 and COL1A2 genes of type I collagen. Most cases of OI type I appear to result from heterozygous mutations in the COL1A1 gene that decrease collagen production but do not alter primary structure, i.e., heterozygous null mutations affect COL1A1 expression.

A third, important example is osteoporosis. The term osteoporosis refers to a heterogeneous group of disorders characterized by decreased bone mass and fractures. An estimated 20-25 million people are at increased risk for fracture because of site-specific bone loss. Risk factors for osteoporosis include increasing age, gender (more females), low bone mass, early menopause, race (Caucasians), low calcium intake, reduced physical activity, genetic factors, environmental factors (including cigarette smoking and abuse of alcohol or caffeine), and deficiencies in neuromuscular control that create a propensity to fall.

More than a million fractures in the USA each year can be attributed to osteoporosis, and in 1986 alone the treatment of osteoporosis cost an estimated 7-10 billion health care dollars. Demographic trends (i.e., the gradually increasing age of the US population) suggest that these costs may increase to $62 billion by the year 2020. Clearly, osteoporosis is a significant health care problem.

Clinically, osteoporosis is segregated into type I and type II. Type I osteoporosis occurs predominantly in middle aged women and is associated with estrogen loss at the menopause, while osteoporosis type II is associated with advancing age. Much of the morbidity and mortality associated with osteoporosis results from immobilization of elderly patients following fracture.

Current therapies for osteoporosis patients focus on fracture prevention, not fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy. thus, the osteoporotic patient population would benefit from new therapies designed to strengthen bone and speed up the fracture repair process, thus getting these people on their feet before the complications arise.

A fourth example is related to bone reconstruction and, specifically, the ability to reconstruct defects in bone tissue that result from traumatic injury; as a consequence of cancer or cancer surgery; as a result of a birth defect; or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate. Toriumi et al. have written the "Reconstructive surgeons should have at their disposal a bone substitute that would be reliable, biocompatible, easy to use, and long lasting and that would restore mandibular continuity with little associated morbidity."

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

VII. Polymers for Implanting of Bone Cell Spheroids

Over the last decade there has been a tremendous increase in applications for polymeric materials. These materials are well suited to implantation as they can serve as a temporary scaffold to be replaced by host tissue, degrade by hydrolysis to non-toxic products, and be excreted, as described by Kulkarni et al. (1971) and Hollinger and Battistone (1986).

Either natural or synthetic polymers can be used to form the matrix, although synthetic polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), and other poly(alpha-hydroxy acids), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, and nylon. Although non-degradable materials can be used to form the matrix or a portion of the matrix, they are not preferred. Examples of natural polymers include proteins such as albumin, fibrin or fibrinogen, collagen, synthetic polyamino acids, and prolamines, and polysaccharides such as alginate, heparin, and other naturally occurring biodegradable polymers of sugar units.

Four polymers widely used in medical applications are poly(paradioxanone) (PDS), poly(lactic acid) (PLA), poly (glycolic acid) (PGA), and PLAGA copolymers. Copolymerization enables modulation of the degradation time of the material. By changing the ratios of crystalline to amorphous polymers during polymerization, properties of the resulting material can be altered to suit the needs of the application. These polymers, including poly(lactide-co-glycolic) acid (PLGA), have been used as polymer composites for bone replacement as reported by Elgendy et al. (1993). Substituted polyphosphazenes have been shown to support, osteogenic cell growth, as reported by Laurencin et al. (1993). Poly(organophosphazenes) are high molecular weight polymers containing a backbone of alternating phosphorus and nitrogen atoms. There are a wide variety of polyphosphazenes, each derived from the same precursor polymer, poly(dichlorophosphazene). The chlorine-substituted species can be modified by replacement of the chlorine atoms by different organic nucleophiles such as o-methylphenoxide along with amino acids. The physical and chemical properties of the polymer can be altered by adding various ratios of hydrolytic sensitive side chains such as ethyl glycinate, as described by Wade et al. (1978) and Allcock and Fuller (1981). This will affect the degradation of the polymer as an implantable and biodegradable material as well as vary the support of osteogenic cells for bone and tissue implants, as shown by Laruencin et al. (1993).

PLA, PGA and PLA/PGA copolymers are particularly useful for forming the biodegradable matrices. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. patents, the teachings of which are hereby incorporated by reference, describe in detail suitable polylactides, their properties and their preparation: U.S. Pat. Nos. 1,995,970; 2,703,316; 2,758,987; 2,951,828; 2,676,945; 2,683,136; and 3,531,561. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture," Chemistry and Industry, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. Poly(lactide-co-glycolide) (50:50), degrades in about six weeks following implantation.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

These polymers are particularly useful in forming fibrous or sponge type matrices for implantation. Polymers can also be used to form hydrogels in which the cells are suspended and then implanted.

A. Other Matrix Materials

Another class of materials for making the matrix is hydroxyapatite, or a similar ceramic formed of tricalcium phosphate (TCP) or calcium phosphate ($CaPO_4$). Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites.

In general, the crystals of pure synthetic apatites, geological apatites and many impure synthetically produced apatites are larger and more crystalline than the biological crystals of bone, dentin, cementum and cartilage. The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. The synthetic materials are highly diverse, as reported in the literature. For example, the characterization of four commercial apatites was reported by Pinholt et al. (1992); Marden et al. (1990) reports on a protein, biodegradable material; Pinholt et al. (1991) reports on the use of a bovine bone material called Bio-Oss™; Friedman et al. (1991) and Costantino et al. (1991) report on a hydroxyapatite cement; Roesgen (1990) reports on the use of calcium phosphate ceramics in combination with autogenic bone; Ono et al. (1990) reports on the use of apatite-wollastonite containing glass ceramic granules, hydroxyapatite granules, and alumina granules; Passuti et al. (1989) reports on macroporous calcium phosphate ceramic performance; Harada (1989) reports on the use of a mixture of hydroxyapatite particles and tricalcium phosphate powder for bone implantation; Ohgushi et al. (1989) reports on the use of porous calcium phosphate ceramics alone and in combination with bone marrow cells; Pochon et al. (1986) reports on the use of beta-tricalcium phosphate for implantation; and Glowacki et al. (1985), reports on the use of demineralized bone implants.

As used herein, all of these materials are generally referred to as "hydroxyapatite". In the preferred form, the hydroxyapatite is particles having a diameter between approximately ten and 100 microns in diameter, most preferably about 50 microns in diameter.

Calcium phosphate ceramics can be used as implants in the repair of bone defects because these materials are non-toxic, non-immunogenic, and are composed of calcium and phosphate ions, the main constituents of bone (Frame, 1987; Parsons et al., 1988). Both tricalcium phosphate (TCP) $Ca_3(PO_4)_2$ and hydroxyapatite (HA) $Ca_{10}(PO_4)_6(OH_2)$ have been widely used. Calcium phosphate implants are osteoinductive, and have the apparent ability to become directly bonded to bone. As a result, a strong bone-implant interface is created.

Calcium phosphate ceramics have a degree of bioresorbability which is governed by their chemistry and material structure. High density HA and TCP implants exhibit little resorption, while porous ones are more easily broken down by dissolution in body fluids and resorbed by phagocytosis. However, TCP degrades more quickly than HA structures of the same porosity in vitro. HA is relatively insoluble in aqueous environments. However, the mechanical properties of calcium phosphate ceramics make them ill-suited to serve as a structural element under load bearing circumstances. Ceramics are not preferred since they are brittle and have low resistance to impact loading.

B. Polymers for Forming Hydrogels

Polymers that can form ionic hydrogels which are malleable can also be used to support the cells. Injecting a suspension of cells in a polymer solution may be performed to improve the reproducibility of cell seeding throughout a device, to protect the cells from shear forces or pressure induced necrosis, or to aid in defining the spatial location of cell delivery. The injectable polymer may also be utilized to deliver ells and promote the formation of new tissue without the use of any other matrix. In a preferred embodiment, the hydrogel is produced by cross-linking the ionic salt of a polymer with ions, whose strength increases with either increasing concentrations of ions or polymer. The polymer solution is mixed with the cells to be implanted to form a suspension, which is then injected directly into a patient prior to polymerization of the suspension. The suspension subsequently polymerizes over a short period of time due to the presence in vivo of physiological concentrations of ions such as calcium in the case where the polymer is a polysaccharide such as alginate.

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate (HEMA), which are crosslinked ionically, and block copolymers such as Pluronics™ or Tetronics™, polyethylene oxide-polypropylene glycol block copolymers which are crosslinked by temperature or pH, respectively.

Other materials include proteins such as fibrinogin, collagen, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly (vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883. Described therein is an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolyrically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005M have been demonstrated to cross-link the polymer. Higher concentrations are limited by the solubility of the salt. The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine), examples of synthetic polyamines are: polyethyleneimine, poly(vinylamine), and poly(allyl amine). There are also natural polycations such as the polysaccharide, chitosan. Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

VIII. DNA Vectors

DNA vectors form important further aspects of the present invention. The use of these vectors to express RNA and/or proteins to enhance the formation of bone cell spheroids ex vivo is specifically contemplated by the present invention. Preferred proteins for expression include members of the TGF-β gene superfamily, including TGF-β1, TGF-β2, TGF-β1.2, BMP-2, BMP-4 and BMP-7, other growth factors such as PTH, extracellular matrix molecules, or cytoadhesion molecules. The term "expression vector or construct" means any type of genetic construct containing a nucleic acid coding for a gene product in which part or all of the nucleic acid encoding sequence is capable of being transcribed into mRNA. The transcript may be translated into a protein, but it need not be. Thus, in certain embodiments, expression includes both transcription of a gene and the translation of its RNA into a gene product (protein). In other embodiments, expression only includes transcription of the nucleic acid, for example, to generate antisense constructs.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with a gene encoding a bone cell spheroid enhancing protein, as may be obtained by isolating the 5' non-coding sequences located upstream of the coding segment or exon, for example, using recombinant cloning and/or PCR technology, in connection with the compositions disclosed herein.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

Of particular use are promoters and enhancers that direct transcription of genes that are specific for or highly expressed in bone tissue, osteoblasts and bone precursor cells. For instance, the promoter and enhancer elements of type I collagen, alkaline phosphatase, other bone matrix proteins such as osteopontin, osteonectin and osteocalcin, as well as c-Fos, which is expressed in large amounts in bone and cartilaginous tissues in the generation process, would all be useful for the expression of bone cell spheroid enhancing constructs of the present invention.

In various other embodiments, the human cytomegalovirus (CMV) immediate early gene promoter, the SV40 early promoter and the Rous sarcoma virus long terminal repeat can be used to obtain high-level expression of nucleic acids. The use of other viral or mammalian cellular or bacterial phage promoters which are well-known in the art to achieve expression are contemplated as well, provided that the levels of expression are sufficient for a given purpose.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotides leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

It is proposed that proteins, polypeptides or peptides may be co-expressed with other selected proteins, wherein the proteins may be co-expressed in the same cell or a gene may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both a bone cell spheroid enhancing gene and the other selected protein in the same recombinant cell.

IX. Methods of Gene Transfer

In order to mediate the effect transgene expression in a cell, it will be necessary to transfer the expression vectors of the present invention into a cell. Such transfer may employ viral or non-viral methods of gene transfer. This section provides a discussion of methods and compositions of gene transfer.

A. Viral Vector-Mediated Transfer

The bone spheroid enhancing constructs may be incorporated into an infectious particle to mediate gene transfer to a cell. Additional expression constructs as described herein may also be transferred via viral transduction using infectious viral particles, for example, by transformation with an adenovirus vector of the present invention as described herein below. Alternatively, lentiviral, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral vectors, as discussed below.

Adenovirus. Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated Virus. AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1995; Chatterjee et al., 1995; Ferrari et al., 1996; Fisher et al., 1996; Flotte et al., 1993; Goodman et al., 1994; Kaplitt et al., 1994; 1996; Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Lentivirus. Lentivirus vectors based on human immunodeficiency virus (HIV) type 1 (HIV-1) constitute a recent development in the field of gene therapy. A key property of HIV-1-derived vectors is their ability to infect nondividing cells. High-titer HIV-1-derived vectors have been produced. Examples of lentiviral vectors include White et al. (1999), describing a lentivirus vector which is based on HIV, simian immunodeficiency virus (SIV), and vesicular stomatitis virus (VSV) and which we refer to as HIV/SIVpack/G. The potential for pathogenicity with this vector system is minimal. The transduction ability of HIV/SIVpack/G was demonstrated with immortalized human lymphocytes, human primary macrophages, human bone marrow-derived CD34 (+) cells, and primary mouse neurons. Gasmi et al. (1999) describe a system to transiently produce HIV-1-based vectors by using expression plasmids encoding gag, pol, and tat of HIV-1 under the control of the cytomegalovirus immediate-early promoter.

Other Viral Vectors. Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

B. Non-Viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the bone cell spheroid enhancing construct may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

X. Modulators and Screening Assays

In still further embodiments, the present invention provides methods for identifying new compounds that modulate bone cell spheroid formation. "Modulating compounds" or "compounds that modulate bone cell spheroid formation" are meant to refer to substances that enhance, inhibit, or alter the ex vivo formation of bone cell spheroids or subsequent microspicule (bone) formation. Such altered activity includes, but is not limited to, changes in timing or extent of bone cell spheroid formation that may occur. Modulating compounds may also substitute for the activities supplied by osteogenic growth factor.

Modulators identified will have utility in methods involved in bone formation, and are also contemplated for therapeutic uses. Modulators that affect bone formation ex vivo in the assays described in the present invention are also contemplated to affect bone formation in vivo. For example, the ability to specifically modulate bone formation would be beneficial for several bone diseases and defects, as described elsewhere in the present invention. Further, the impact of any possible adverse effects by a modulator can be limited or otherwise controlled by the more specific administration of the modulator to a specific location.

It is further contemplated that useful compounds in this regard will in no way be limited to proteinaceous or peptidyl compounds. In fact, it may prove to be the case that the most useful pharmacological compounds for identification through application of the screening assays will be non-peptidyl in nature and, e.g., which will serve to modulate bone cell spheroid or microspicule (bone) formation through a tight binding or other chemical interaction. Candidate substances may be obtained from libraries of synthetic chemicals, or from natural samples, such as rain forest and marine samples.

A. Modulation of Bone Cell spheroid Formation

The present invention also concerns a method for identifying a modulator of mammalian bone formation by the steps of obtaining an osteogenic or bone precursor cell; culturing the cell under serum free conditions in the presence of a candidate modulator in the absence osteogenic growth factors; measuring bone cell spheroid formation; and comparing the formation of bone cell spheroid with that observed in the absence of the modulator. Bone cell spheroid and microspicule formation in this assay will be compared to that of a osteogenic or bone precursor cell cultured in the presence of one or more osteogenic growth factors. In another embodiment, the present invention concerns a method for identifying a modulator of bone formation by obtaining an osteogenic or bone precursor cell; culturing said cell under serum free conditions in the presence of a candidate modulator in the presence of one or more growth factors of the TGF-β gene superfamily; measuring bone cell spheroid formation; and comparing the formation of bone cell spheroid with that observed in the absence of the modulator. Modulators identified by this assay would be expected to enhance, inhibit or act synergistically with growth factors such as those of the TGF-β gene superfamily.

B. Second Generation Modulators

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

Certain compounds that mimic elements of protein secondary structure are designed using the rationale that the peptide backbone of proteins exists chiefly to orient amino acid side chains in such a way as to facilitate molecular interactions. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of computer-based chemical modeling is now well known. Using such methods, a chemical that specifically modulates bone cell spheroid formation can be designed, and then synthesized, following the initial identification of a compound that modulates bone cell spheroid formation, but that is not specific or sufficiently specific to other human or animal bone formation properties. It will be understood that all such sterically similar constructs and second generation molecules fall within the scope of the present invention.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Culture of Osteogenic Cells and Cell Lines. Osteogenic cell lines such as human osteosarcoma cells (MG63) were cultured in RPMI 1640 (Gibco, Grand Island. N.Y.) containing 2 mM L-Glutamine, sodium pyruvate and 10% Fetal Calf Serum (FCS) (Hyclone Labs Inc., Logan, Utah). For bone cell spheroid formation, cells were grown to confluency, trypsinized, washed two times in RPMI, and immediately cultured in serum-free media containing 1% ITS+ (Collaborative Research Inc.) and 200 pM TGF-β1 (Collaborative). Unless otherwise noted, cells are plated at a density of about $10^3$ to $10^6$ cells/cm$^2$ in tissue culture dishes. Control cells were allowed to adhere to plastic for 3-4 hours in serum containing medium following trypsinization. This adherent cell layer was then washed twice with serum-free medium and cultured as above with or without TGF-β1.

Human Bone Precursor Cells (HBPC). Purified populations of HBPC were isolated from human bone marrow as described previously (Long et al., 1995). Human bone marrow was obtained from normal volunteers. Briefly, mononuclear cells were prepared from human bone marrow by separation on ficoll (Sigma, St Louis, Mo.), and low-density cells cultured overnight culture to remove plastic-adherent cells. Non-adherent low-density cells were collected and allowed to undergo immune adhesion to anti-Osteonectin (ON) and anti-Osteocalcin (OC) antibodies immobilized on plastic as described (Long et al., 1995). The immune adherent cells were collected by trypsinization.

Primary Human Osteoblasts. The isolation procedure was essentially that of Robey and Termaine (1985). Briefly, human bone chips were obtained (following informed consent and IRB approval) during orthopedic surgery. These were treated with Collagenase D (Boehringer Mannheim, Mannheim, Germany) for 2 hrs at 37° C., the non-adherent cells washed off, the bone pieces minced, and cultured in Ca$^{2+}$—free DMEM (Gibco, Grand Island, N.Y.) containing 10% FCS and Pen/Strep. After the cultures were confluent, the cells were collected by trypsinization and cultured in Ca$^{2+-}$ containing DMEM for 2-3 weeks. Bone-derived osteoblasts were recovered by trypsinization and centrifugation.

Bone Cell-Spheroid Formation. In order to induce three-dimensional cell development (i.e., bone cell spheroids), cells were trypsinized as routinely performed for passage, the trypsin inactivated by serum addition, the cells washed three times, and immediately cultures in RPMI/ITS$^+$ (see above) containing 200 pM TGF-β1, Control cells were allowed to adhere to plastic for 3-4 hours in serum containing medium following trypsinization. This adherent cell layer was then washed twice with serum-free medium and cultured as above with or without TGF-β1.

Collagen Synthesis. At the times indicated, bone cell-spheroids were washed with prolene-free DMEM containing 1% ITS, and incubated for 12 hours in the presence of ITS$^+$ and 100 μCi/ml ($^3$H) Proline (Amersham). Cells and medium were harvested, and cell lysates were made. Protein content was estimated by the BCA method (Smith, 1985), using a kit from Pierce (Rockford, Ill.). The cell lysates were lyophilized and extracted overnight at 4° C. with 0.5M acetic acid containing 100 μg/ml pepsin (Sigma Chemical Co., St. Louis, Mo.). Samples were dried, dissolved in non-reducing SDS-gel buffer and analyzed on a 5% SDS-gel. The $α_1(1)$ and $α_1(111)$ components were resolved by delayed reduction electrophoresis (Sykes, 1976). The gels were treated with Amplify (Amersham, England), and the radiolabeled collagen visualized by autoradiography. The percentage of Type I collagen was determined using the following formula (Franceschi, 1988).

$$\% \text{ Type } 1 = \frac{(α_1(1)/2) \times 100}{α_1(1)/2 + α_1(111)/3}$$

Western Analysis. The procedure used was essentially that of Towbin (1979). Samples were run on a 10% SDS-PAGE. The electrophoretically resolved proteins were transferred to nitrocellulose (Schleicher & Schuell; Keene, N.H.) and the nonspecific binding sites blocked using 5% Skim milk in TBST (10 mM Tris, 0.15M NaCl, 0.05% Tween 20, pH 7.5). The nitrocellulose membrane was incubated with primary antibodies: anti-Osteonectin (ON), anti-alkaline phosphatase, (both generous gifts of Dr. Kenneth Mann, University of Vermont) or anti-Type I collagen (Collaborative); each at 10 μg/ml in TBST) for 1 hour at room temperature, washed with TBST and treated with the secondary antibody (anti-mouse IgG-HRP conjugated; Amersham) at a 1:1000 dilution in the same buffer. The HRP/anitbody-labeled proteins were visualized by enhanced chemilluminescence (Pierce).

Alkaline Phosphatase Assays (Elias, 1982). At the indicated time points, bone cell-spheroids were collected, washed two times with PBS, and centrifuged at 400 for 6 minutes. The cells were lysed (1.5M Tris HCl, 1 mM ZnCl$_2$, 1 mM MgCl$_2$.6H$_2$O, pH 9.2, 1% TritonX100) at 4° C. for 30 minutes. Alkaline Phosphatase activity was determined by the colorimetric method using a kit (Sigma). The activity was expressed as μmol of para-nitrophenol formed/hour/mg protein.

Immunocytochemical and Histochemical Staining Procedures. Cytocentrifuge preparations were made from TGF-β1 induced cell spheroids, and the osteonectin (anti-ON, 10 μg/ml), alkaline phosphatase, and Type I collagen (anti-Coll I, Sigma) proteins detected using an avidin-biotin based immunocytochemistry ABC immunochemical staining kit (Pierce) as described elsewhere (Long, 1990). Collagen also was detected by the Masson's staining procedure (Gomori, 1950; Lillie, 1940, purchased from Sigma, St. Louis). Histochemical Alkaline Phosphatase activity was determined per manufactures instructions (Sigma). Finally, mineralization of the cultures was determined by the Alizarin Red S (Sigma) staining procedure (pH 5) (McGee and Russell, 1958).

Flow Cytometric Analysis: Bone cell spheroids formed from MG63, HBPCs, or primary Osteoblasts were disaggregated with trypsin followed by treatment with 2 mg/ml Collagenase D (Boehringer Mannheim). Trypsin enzymatic activity was stopped by the addition of 10% FCS. Cells were visualized by indirect immunofluorescence and analyzed using a FACSCAN flow cytometer (Becton Dickinson, Mountain View, Calif.). The primary antibodies were monoclonal anti-human α2, α3, α4, α5, β3, or β1 integrins (from either Becton & Dickinson, San Jose, Calif., or from GIBCO). The secondary antibody was FITC-conjugated anti-mouse IgG (Sigma). Antibody controls were isotype-specific inappropriate antibodies.

Inhibition of Cell Condensation. Cells were cultured in serum-free media under conditions that establish bone cell spheroids (as described above) in the presence of neutralizing antibodies to α2, α3, and/or β1 integrins, at 10 μg/ml. Isotype-specific inappropriate antibodies served as negative controls. Antibodies were added every second day over a seven-day culture period. EGTA (0.5 mM) was also used inhibition of cell aggregation, as was puromycin (5 μM).

Raman Spectroscopy. Cell spheroids containing microspicules were examined intact or treated with trypsin to remove the cells. Trypsinized samples were repeatedly washed in methanol to remove surface organics, the microspicule samples were mounted onto quartz slides, any remaining methanol allowed to evaporate, and then covered with a quartz coverslip. Sample thickness varied from sample to sample. Multiple Raman spectra (i.e., 150 to 350 spectra) were acquired at 2 μm intervals along a randomly selected line. A 785 nm laser (SDL, Inc.) is used as the excitation source and the laser spot is transferred into an epi-fluorescence microscope (Olympus BH-2) equipped with either a 10x/0.5 NA or a 20x/0.75 NA Fluar objective (Zeiss). The sample is translated by an X-Y translation stage (New England Affiliated Technologies, Inc.) capable of 0.125-μm steps. Raman scatter was collected and transferred to an axial-transmissive spectrograph (Kaiser Optical systems, Inc. Holospec F/1.8i) for dispersion. The detector was a liquid $N_2$-cooled backthinned CCD camera (Princeton Instruments, Inc.). For the intact (non-trypsinized) samples, Raman scatter was transferred to an axial-transmissive spectrograph (Kaiser Optical systems, Inc. Holospec VPT series) and the detector was a water-cooled (−20° C.) CCD camera (Andor, Inc.). The spectrograph was calibrated with an argon or neon emission lamp. Comparison of intact and trypsinized samples demonstrated that intact cell-spheroids/microspicules obscured certain components of the Raman spectra. As a result, the data is present only for trypsinized samples. Raman point spectra were collected every 2-μm with an integration time of 15 to 30 seconds. Slit widths of 25-μm gave a spectral resolution of the order of 4 cm$^{-1}$. Data analysis was performed in Matlab (Mathworks, Inc.) using in-built and locally written functions. Data was stored on a Pentium-based computer.

The multiple spectra acquired from microspicules consisted of 150-350 randomly acquired spectra (known as Raman transects) measured along a line across each microspicule. These spectra were analyzed using Factor Analysis, a multi-variant statistical analysis in which the data are reduced to a specific number of (fewer) linear combinations, or factors, that describe the data. This statistical approach is a powerful means of "averaging" spectra (i.e., extracting component spectra) as it does not require prior knowledge of the nature of the pure constituent spectra. In many cases, several factors were needed to fully represent the data set. Typically, 3 to 6 factors, including background factors, were required to represent greater than 99.9% of the total variance of the data set. More factors were not included in the analysis as, in many instances, the remainder consisted of descriptions of noise in the data set.

Transmission Electron Microscopy. Bone cell spheroids formed from primary osteoblasts were processed for TEM, using standard procedures (Hayat, 1989). Briefly, samples were fixed in 2% glutaraldehyde and post-fixed in 1% osmium tetroxide. Following steps of dehydration, samples were embedded in Epon, sectioned, stained and observed on the Phillips CM 100 Electron microscope, Mahwah, N.J.

Example 2

Formation of Bone Cell Spheroids and Microspicules

Given the role of cellular condensation in chondro/osteogenesis both in vivo (Hall and Miyake, 1995; Dunlop and Hall, 1995) and in vitro (Denker, 1995), the inventors reasoned that similar processes are involved in the ex vivo formation of human bone. To examine this hypothesis, the inventors utilized three populations of human osteogenic cells: the MG63, preosteoblastic osteosarcoma cell line (Franceschi, 1985) and other cell lines such as 3T3, SAOS2, and C310T1/2, immunologically purified human bone precursor cells (HBPC; a population of preosteoblast-like cells) (Long, 1995) and osteoblasts derived from collagenase-treatment of bone fragments (Robey and Termine, 1985 and Table 1). The inventors observed that serum-free treatment of these cell types with TGF-β1 immediately following trypsinization and subsequent serum-free culture results in the formation of three-dimensional, spherical cellular condensates (cell spheroids) within 24-48 hours (FIG. 1, top Row). Consistent with the induction of differentiation, spheroid-formation also induces a cessation of proliferation in each cell type. As a result, spheroids develop as a consequence of cell-cell interactions (see below) and not proliferation. During the first 24 hours of TGF-β treatment, the cells re-adhere, and between 24-48 hours detach from the tissue culture plastic to form cell-spheroids. Bone-cell spheroids are not formed if the cells are cultured in the absence of TGF-β1, if the cells are first allowed to adhere to plastic in the presence of serum (i.e., as typically passaged), or if the serum-containing medium used to passage the cells is subsequently (i.e., after 24 hrs) replaced with serum-free media containing TGF-β1 (controls). Spheroid formation is dependent on protein synthesis as it is completely blocked by puromycin treatment. It is also inhibited by the presence EGTA, suggesting a role for calcium-dependent adhesion molecules in spheroid formation (EGTA and puromycin data below).

TABLE 1

Tissue Sources and Cell Lines Producing Bone Ex vivo

| Cell Source | Phenotype/Source | Micro spicule Formation |
| --- | --- | --- |
| Human Preosteoblasts/Osteoblasts | Collagenase Treated Bone | ++++ |
| Human Bone Precursor Cells | Bone Marrow | +++ |
| MG63 Cells | Human Osteosarcoma | ++ |
| C3H10T1/2 Cells | Murine Mesoderm | ++ |
| SAOS2 Cells | Human Osteosarcoma | + |
| Hep2G Cells | Hepatoma | neg. |
| A549 Cells | Human Embryonic Lung | neg. |
| NIH3T3 Cells | Murine Fibroblasts | neg. |
| KG1a Cells | Human Myeloid | neg. |

Figure 2:
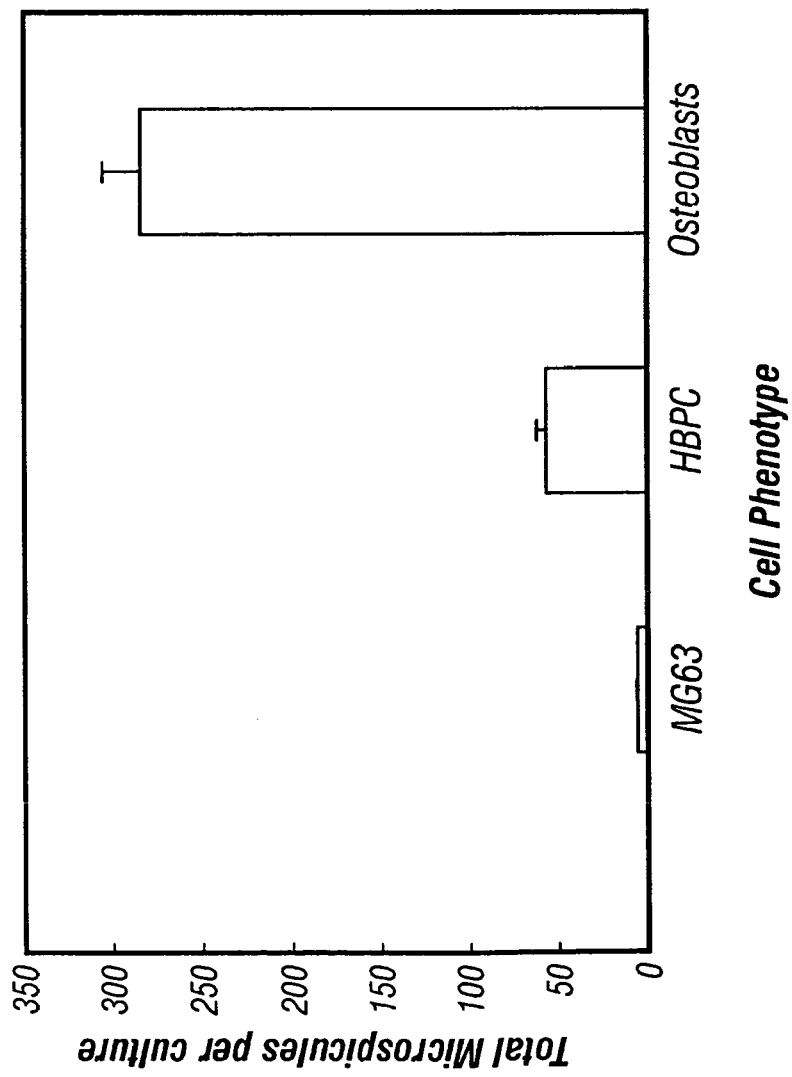
FIG. 2. Microspicule Formation is Dependent on Bone Cell Phenotype. Total number of microspicules formed per by each of the three cell types studied. Values are mean±SD.

Within three-five days of spheroid-formation, the cellular spheroids begin to form small bone-like crystalline structures (termed microspicules; FIG. 1, row 2). Microspicules continue to develop until days 7-10. The ability to form spheroids and microspicules is restricted to those cells having osteogenic potential (Table 1), and is proportionate to both the approximate developmental status of the osteogenic cells and their cell plating density (below). Thus, the osteoprogenitor-like MG63 cells form the fewest microspicules (FIG. 2). The early preosteoblast-like human bone precursor cells form intermediate numbers of microspicules. The bone-derived osteoblasts show a seven-fold increase in microspicule formation (compared to MG63 cells), with each cell-spheroids producing a microspicule.

Example 3

Analysis of Human Bone Formation Ex vivo

Figure 3:
FIG. 3. TEM Analysis of Bone Cell Spheroids and Microspicules. Primary osteoblasts were cultured under cell spheroid forming conditions. The upper panel shows a section through the microspicule (MSp) with the cuboidal osteoblasts lining the MSp These cells show a prominent nucleus (N), and long cellular processes lining the MSp (magnification 3,000). Higher magnification (middle panel) of a microspicule demonstrates the close apposition of the osteoblasts to the MSp. Arrows point to the cell processes lining the MSp (magnification 15,900). Nucleus (N), mitochondria (M). The lower panel shows the microspicules (MSp) mineralization front (MF) and the 640-670 Å crossbands of collagen (magnification 15,200).

In order to confirm that microspicules are comprised of human bone, the inventors performed a number of cytochemical, immunological, biochemical, and physicochemical analyses. Both spheroids and microspicules from all three cell types express osteonectin (immunocytochemical determination, FIG. 1, Row 3). Collagen is detected by both the Masson's stain (FIG. 1, Row 4) and immunocytochemical detection using anti-human Type-I collagen antibody (FIG. 1, Row 5) The spheroid cells also strongly express alkaline phosphatase enzymatic activity (FIG. 1, Row 6). Finally, Alizarin Red S demonstrates the presence of calcium phosphates within the microspicules of all three-cell types (FIG. 1, Row 7). Similarly, spheroids from each bone cell type-expressed tenascin, bone sialoprotein and osteocalcin (below). The inventors next evaluated the structural relationship between the microspicules and cells within the spheroids. Transmission electron micrograph analysis indicates a close approximation bone-derived osteoblasts to the developing microspicules (FIG. 3A). Long cytoplasmic processes are observed to line the microspicules (FIGS. 3A and 3B). Finally, high-magnification TEM indicates the closeness of the "ineralization front" and the cell surfaces (FIG. 3C). As well, the typical 640-670 Å banding pattern of collagen can be seen within the microspicule.

Figure 4A:
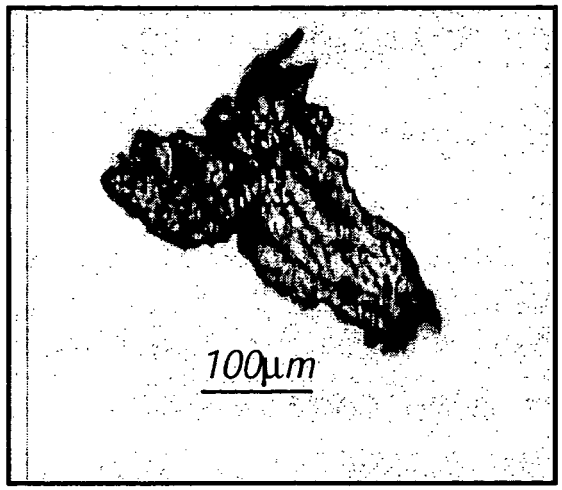
FIG. 4A, FIG. 4B, FIG. 4C and FIG. 4D. Raman Analysis of Microspicules. Bone cell spheroid derived microspicules analyzed by Raman Spectrography as in Methods. A representative bone microspicule is shown in FIG. 4A. The spicule is then crushed between the quartz slide/coverslip and Raman transects of 150-300 spectra acquired (FIG. 4B white cross-hatched line). A representative sample, of three Raman spectra are shown in FIG. 4C. These clearly show the $v_1$ ($PO_4$) band indicative of bone (959 cm$^{-1}$). Factor Analysis (see text) of these spectra (FIG. 4D) indicate a clear $v_1$ ($PO_4$) signal present in both day 3 (upper spectra) and day 7 (lower spectra) microspicules.
Figure 4B:
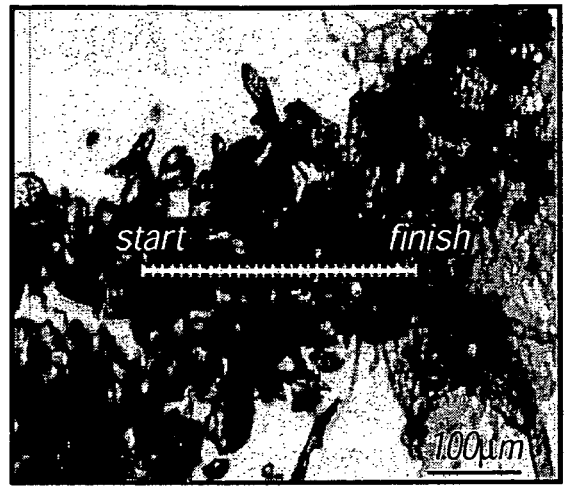
Figure 4C:
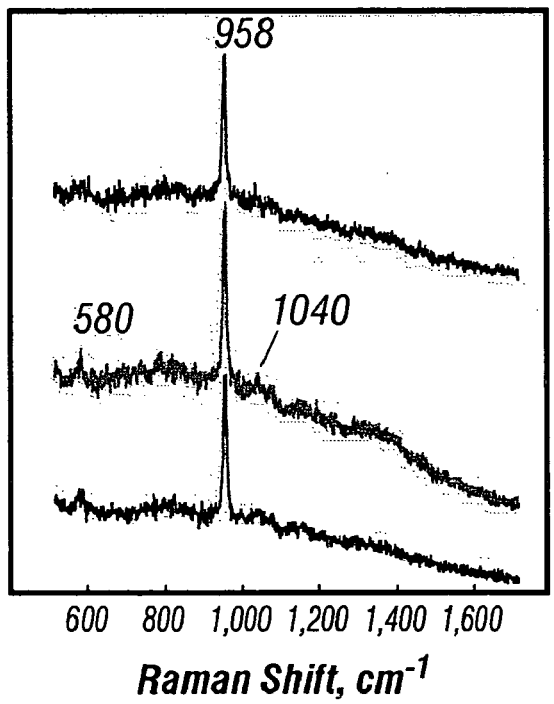
Figure 4D:
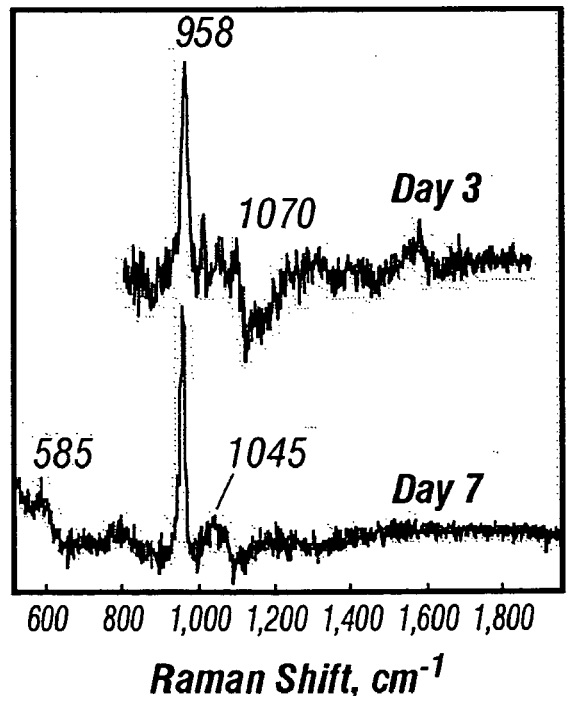

Although the cytochemical, and immunological data are consistent with the process of bone formation, they do not demonstrate the presence of the carbonated apatite seen in human bone. To determine the presence of substituted hydroxyapatite, the inventors utilized physical-chemical determinations. Electron microprobe analysis (EMA) of crushed microspicules indicates a calcium-to-phosphate ratio of 1.67-1.7, which is consistent with that seen in control samples of purified hydroxyapatite. This EMA data was confirmed and extended by Raman spectrographic analysis. Raman spectrograph analysis demonstrates the presence of phosphate-and-carbonate substituted apatitic species that are consistent with the presence of loosely organized bone. Factor Analysis of spectra from microspicules obtained on days 3, 5, and 7 of culture revealed several domains that allowed clear identification of apatitic calcium phosphate and monohydrogen phosphate ions, typical of bone mineral (FIG. 4C). For typical Raman spectra of day 7 samples, the $v_1$ phosphate band at 958 $cm^{-1}$, characteristic of apatitic calcium phosphate, is the strongest peak (FIGS. 4C and 4D). In kinetic analyses, the presence of apatitic calcium phosphate is detected as early as day 3, a period in which microspicules are not readily recognized within the spheroids without trypsinization. These kinetic studies also indicate a narrowing of the $v_1$ phosphate band from approximately 18 $cm^{-1}$ in day 3 samples to approximately 12 $cm^{-1}$ in day 7, demonstrating an increase in the order of the calcium phosphate phase. Such narrowing data is consistent with Fourier Transform Infrared (FT-IR) analyses of the rat growth plate demonstrating an increase in $v_1$ phosphate band sharpness with an increasing mineralization of the hypertrophic zone (Mendelsohn, 1989; Kim et al., 1996; Paschalis et al., 1996). It should be noted that not all day 3 spheroids contain detectable regions of microspicule formation, and that the day 3 calcium phosphate spectrum was apparent only after Factor Analysis. This suggests that the deposition of calcium phosphate tends to cluster in certain regions of the spheroid during the early phases of bone formation.

The concentration of carbonate ions ($CO_3^{2-}$) and monohydrogen phosphate ($HPO_4^{2-}$) ions in the apatitic lattice are markers of bone maturity. In several of the Factor-resolved bone spectra, bands at 1065-1070 $cm^{-1}$ are seen (FIGS. 4C and 4D). These bands are typically assigned to carbonate $v_1$ (C=O) stretches that specifically correspond to Type B carbonate—in which carbonate substitutes for the phosphate ions in the apatite lattice. The intensity of this band is generally weaker than that observed in spectra extracted from mature cortical bone (Rey, 1995 and 1996) indicating a slightly less substituted (i.e., less carbonated) bone mineral. In a few cases, carbonate also is observed as bands at 1110 $cm^{-1}$ and 1150 $cm^{-1}$, typically associated with Type A substituted carbonate—in which carbonate substitutes for monovalent hydroxy ions within the apatitic matrix. These bands were typically less predominant, implying high Type B to Type A carbonate band ratios in these microspicules. Additionally, analysis of the Raman transects indicates regions of substituted apatitic crystal interspersed with areas of amorphous non-crystalline protein. The inventors did not detect a clear collagen signature within the Raman spectra. However, the electron microscopic, biochemical and immunological detection of Type I collagen at all time periods during microspicule formation led to the interpretation that this as a technological (detection) problem, as the degree of mineralization seemingly obscures collagen detection by Raman spectroscopy. This verifies that TGF-β1-driven condensation of bone cells leads to the formation of a microcrystalline, carbonated hydroxyapatite that is consistent with the presence of human bone.

Example 4

Spheroid-Formation Regulates Bone-Related Protein Expression

Figure 5A:
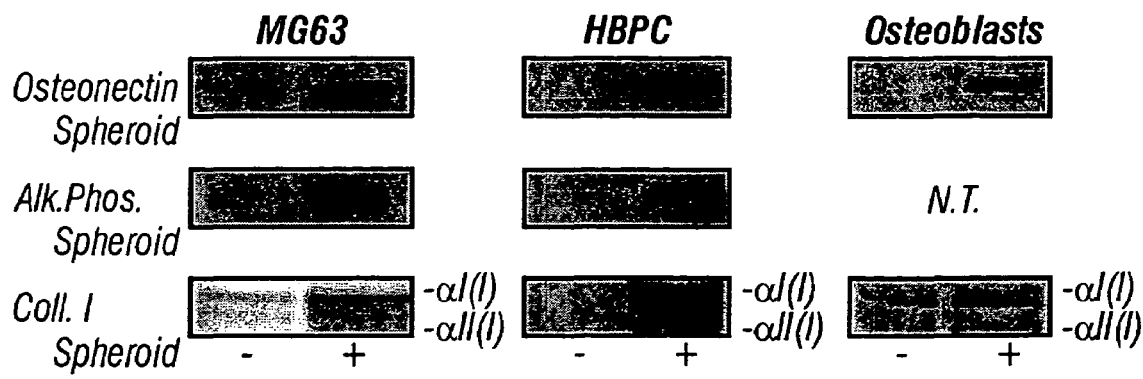
FIG. 5A and FIG. 5B. Bone Protein Expression and Alkaline Phosphatase Activity of Bone Cell Spheroids. Bone cell types were cultured serum free (spheroid-minus) as well as in presence of TGFβ (spheroid-positive) after 1 week of culture.
Figures 1, 5B:
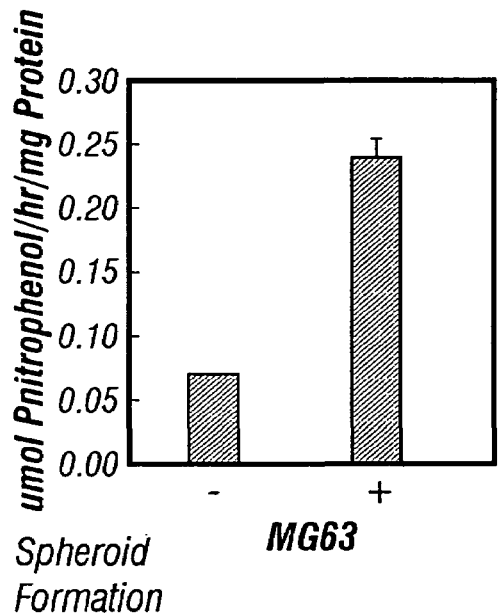
Figures 2, 5B:
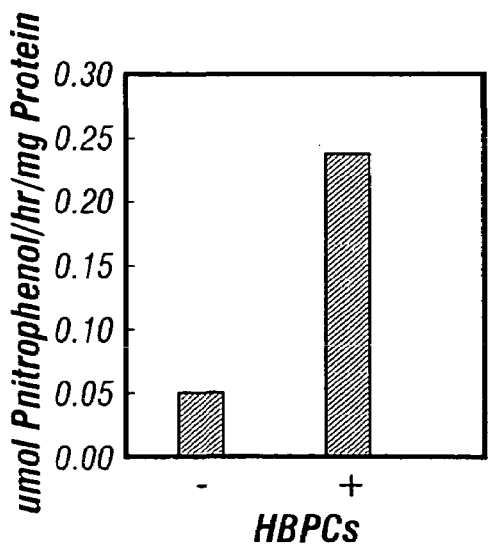
Figures 3, 5B:
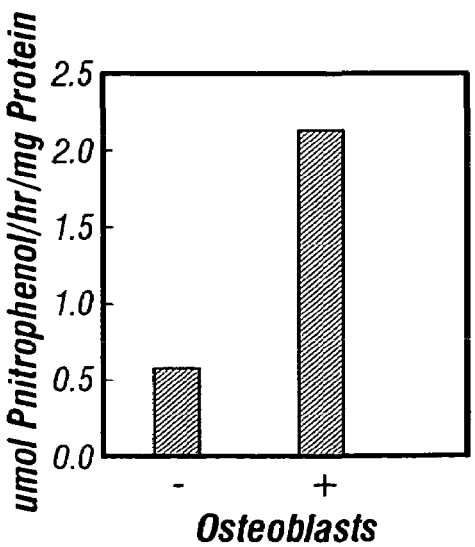

The above cytochemical analyses of bone protein expression in cell-spheroids was confirmed by Western and biochemical analyses. These studies indicate that the process of TGF-β1-dependent bone cell spheroid formation results in increases in the relative abundance of both collagenous and non-collagenous proteins. Western analysis indicates that spheroid-formation in each osteogenic cell type markedly increases expression of osteonectin and alkaline phosphatase (FIG. 5A, top and middle rows) compared to control cells grown under serum-free conditions in the absence of TGF-β1 (that, therefore, do not form spheroids). Collagen synthesis was determined by tritiated-prolene incorporation utilizing delayed-reduction electrophoresis (Sykes, 1976) to distinguish between Type-I and Type-III collagens. Under these electrophoretic conditions, Type-III collagen appears as a single band of αI(III) chains, and Type-I collagen appears as two bands of αI(I) and αII(I) chains, respectively, in a 2.5 to 1 ratio (Franceschi, 1988). The $^3$H-prolene incorporation studies indicate that the collagen produced by all three cell types is greater than 95% Type-I collagen (FIG. 5, bottom row). Both MG63 cells and HBPC cells markedly up-regulate Type-I collagen synthesis following spheroid formation. In contrast, primary osteoblasts isolated from human bone constitutively express Type-I collagen. Nonetheless, TGF-β1-dependent bone cell spheroid formation results in a two to three fold increase in collagen synthesis in these cells (collagen chain ratios and quantitative determinations by densitometry). Bone cell spheroid formation also induces a marked temporal increase in alkaline phosphatase activity for each of the three osteogenic cell types (FIG. 5B). Finally, the inventors evaluated the expression of osteocalcin during spheroid formation. Although small, localized, amounts of this bone protein were detected by immunocytochemistry, we could not confirm its expression by Western analysis. This indicates that osteocalcin is produced in small amounts by these cells, but its presence may not be an obligate requirement for microspicule formation.

Figure 6A:
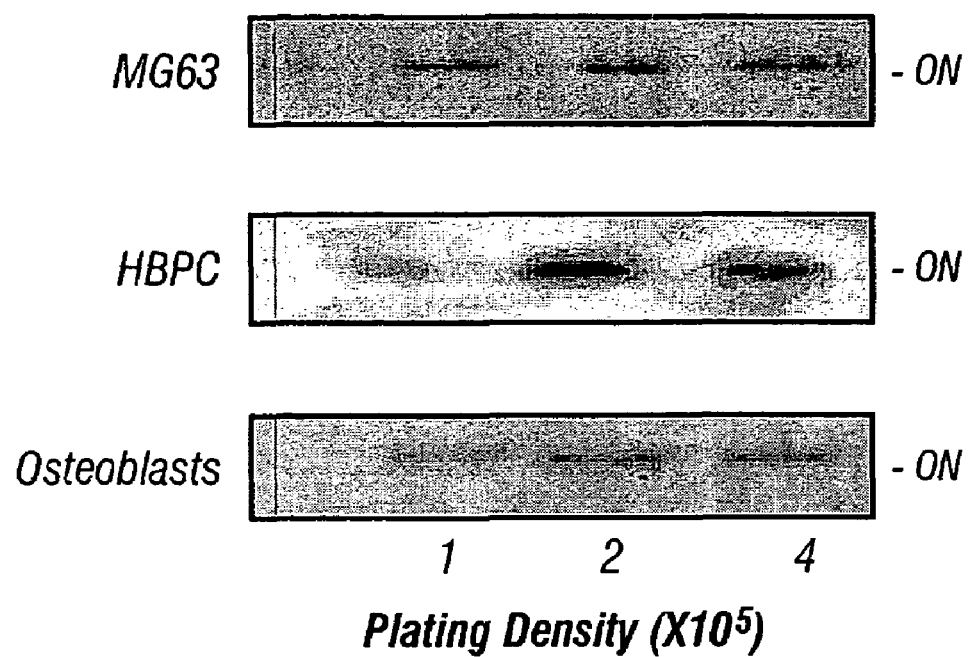
FIG. 6A and FIG. 6B. Density-Dependent Induction of Bone Protein Expression.
Figure 6B:
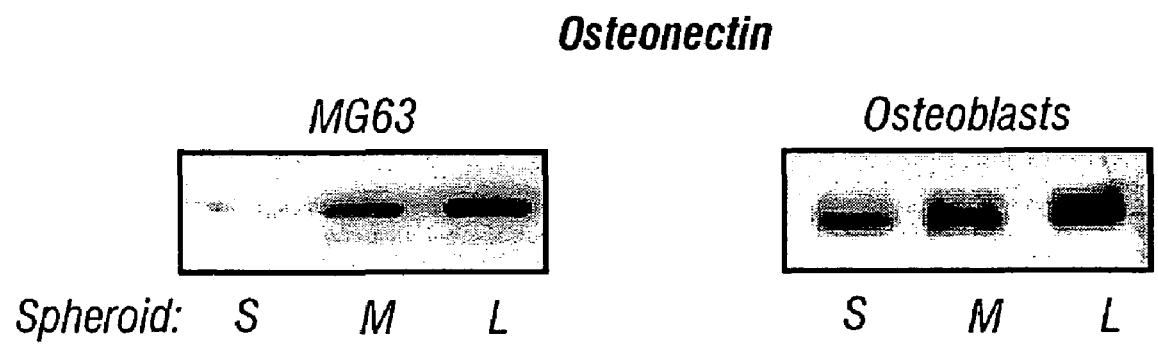

Increasing bone cell density within the spheroids also induces increased expression of non-collagenous proteins. We first noted that the total number of spheroids forming per cultures depended on the initial cell-plating density. For MG63 and collagen-released osteoblasts, the optimal plating density was $2\text{-}4 \times 10^5$ cells (i.e., $0.5\text{-}1.0 \times 10^5$ per $cm^2$), whereas human bone precursor cells required approximately ten times as many cells. These immune-purified cells are approximately 70% pure (Long, 1995), but remain a heterologous cell population, presumably containing other bone marrow derived cells that may modulate microspicule formation. These studies indicated that optimal bone protein induction during spheroid formation (using anti-osteonectin as a probe) occurred at the same optimal plating densities as those required for spheroid formation (FIG. 6A). The inventors therefore isolated and pooled individual spheroids, categorizing them into small, intermediate, and large cell aggregates by visual inspection. The evaluation of osteonectin expression in these isolated bone cell spheroids indicates an increase in relative abundance with an increasing spheroid size (FIG. 6B), consistent with a cell-density mediated process.

Figure 7A:
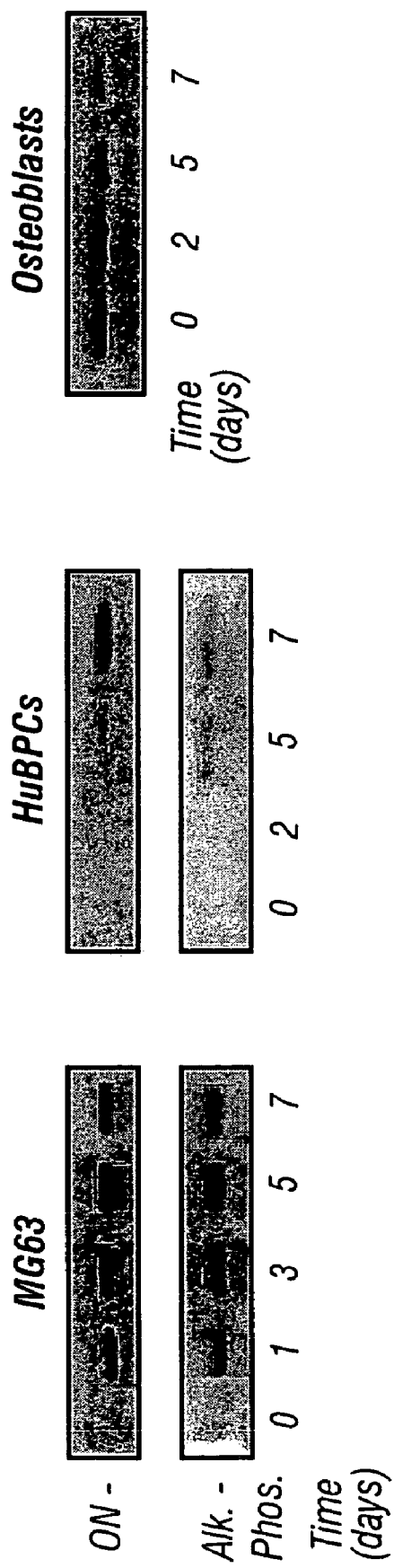
FIG. 7A and FIG. 7B. Kinetics of Bone Protein Expression.
Figures 1, 7B:
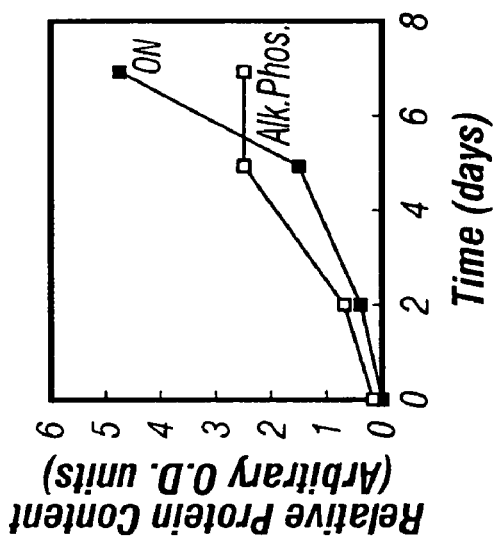
Figures 2, 7B:
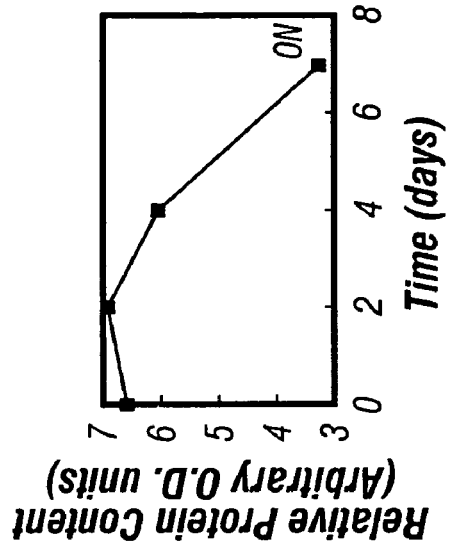
Figures 3, 7B:
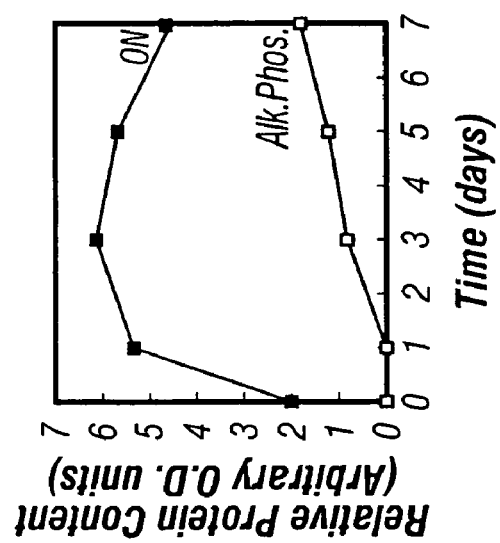
Figures 4, 7B:
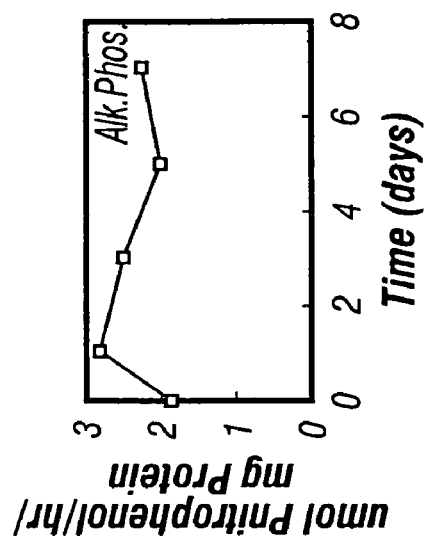

Evaluation of the kinetics of bone protein expression demonstrates distinct temporal differences among the three osteogenic cell types. MG63 cells constitutively express low levels of both osteonectin and alkaline phosphatase (FIGS. 7A and 7B, left panels). Following induction of spheroid formation, osteonectin expression by MG63 cells markedly increases over the first 24 hours, reaches a plateau on Days 3-5, and then moderately decreases in relative abundance. Alkaline phosphatase expression in MG63 cells shows a slow increase over the first three days and continues to increase until Day 7. In human bone precursor cells, both osteonectin and alkaline phosphatase increase for five days, at which point osteonectin sharply increases in relative abundance (FIGS. 7A and 7B, center panels). As expected, collagenase-derived osteoblasts express high levels of enzymatic alkaline phosphatase throughout the period of microspicule formation, although activity falls slightly after one day of culture. Likewise, osteonectin is constitutively expressed by primary osteoblasts, but reduces its relative abundance three to seven days after bone cell spheroid formation (FIGS. 7A and 7B, right panels).

Example 5

Cell:Cell Interactions Mediate Spheroid Formation

Figure 9A:
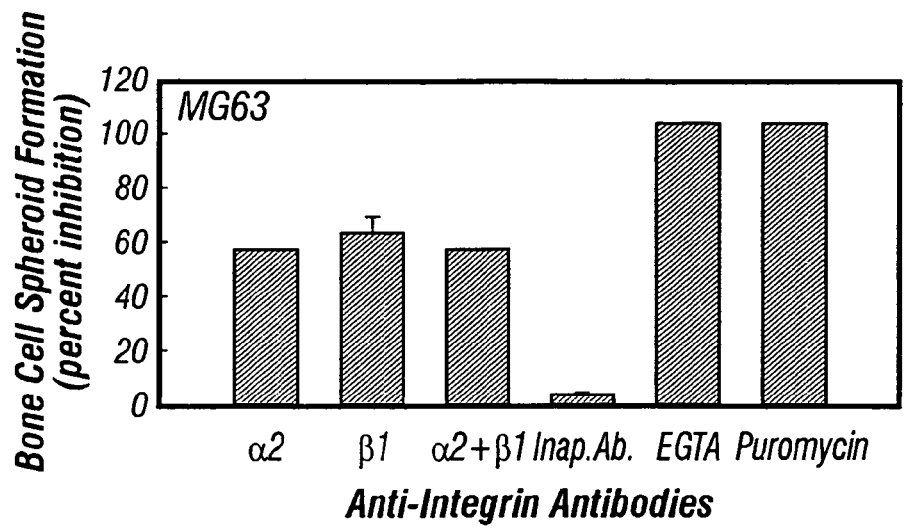
FIG. 9. Inhibition of Bone-Cell Spheroid and Bone Microspicule Formation. Bone cells were grown in cell-spheroid forming conditions in the presence or absence of anti-α2, anti-α3 (for HBPCs), and/or anti-β1 integrin antibodies, each alone and in combination. Controls consist of isotype-specific inappropriate antibodies. Cells also were cultured in presence of EGTA (0.5 mM) or puromycin (5 μM). Percent inhibition is determined compared to control inappropriate antibody controls, or lack of EGTA or puromycin. Inappropriate antibodies do not inhibit spheroid/microspicule formation.
Figure 9B:
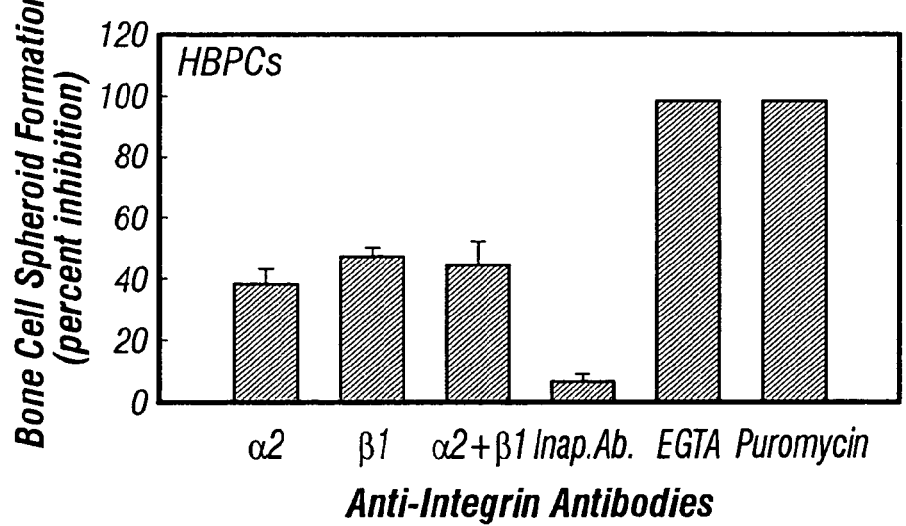
Figure 9C:
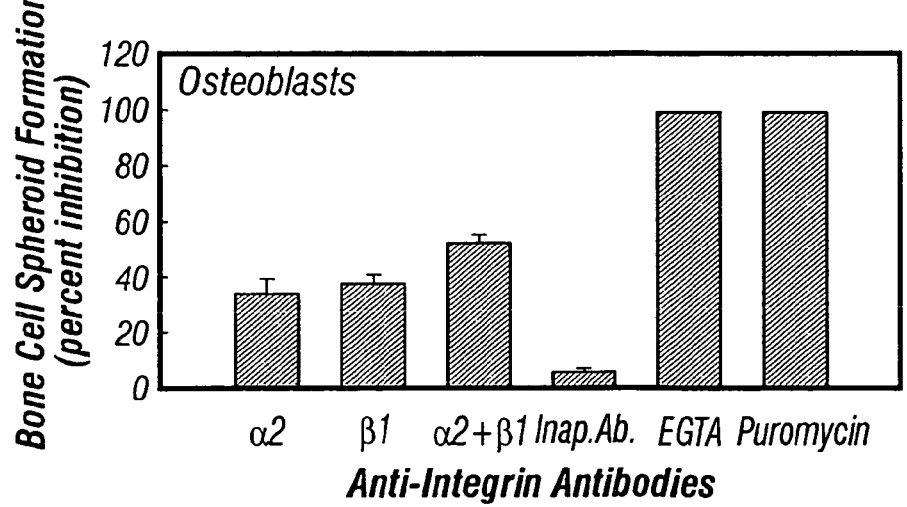

As mentioned, spheroid formation occurs as a consequence of calcium-dependent cell:cell interactions rather than cell proliferation. This implies that cell-surface cytoadhesive ligands and their counter-receptors mediate this process. Evaluation of a number of putative cytoadhesion-molecule targets (e.g., cadherins, selecting, and integrins) indicated that TGF-$\beta$1-induced spheroid formation is mediated by $\beta_1\alpha_3$, and $\beta_1 \alpha_2$ integrins (and that selectins and cadherins are not detected). Flow cytometric analysis of each of the three osteogenic cell types indicated that they constitutively expressed $\beta_1$ integrin (FIG. 8, lower row). Spheroid formation results in the increased expression of $\alpha_2$-integrin in MG63 cells and collagen-released primary osteoblasts, and increases $\alpha_3$-integrin chain expression in human bone precursor cells (FIG. 8, upper row). In order to determine if these integrins mediate cell:cell interactions and subsequent spheroid formation, the inventors utilized neutralizing antibodies to individual integrin chains. For each cell type, inhibition of spheroid formation (and, hence, microspicule development) was observed with anti-$\beta_1$ antibody, or the appropriate anti-$\alpha$ chain antibody (FIG. 9). These antibodies individually caused a 40-60% inhibition in the number of spheroids, and various combinations of these anti-$\alpha$ and anti-$\beta$ integrin antibodies did not further inhibit spheroid number or size, suggesting that the individual antibodies fully saturated the integrin-mediated component of cytoadhesion. Importantly, anti-integrin antibody treatment reduced the cellularity of the spheroids. As a result, few if any of the remaining spheroids produce microspicules. Finally, this bone cell spheroid formation is completely inhibited by inclusion of EGTA or puromycin (FIG. 9).

Example 6

Cytokine Regulation of Osteogenesis

Of the multiple cytokines implicated in osteogenesis, two factors play a central role in bone cell development: TGF-$\beta$ and insulin-like growth factor (IGFs). TGF-$\beta$ is localized in active centers of bone differentiation (cartilage canals and osteocytes), and is found in high quantity in bone, suggesting that bone contains the greatest total amount of TGF-$\beta$. (Massague, 1987) During bone formation, TGF-$\beta$ promotes chondrogenesis (Massague, 1987), an effect presumably related to its ability to stimulate the deposition of matrix components. Ignotz & Massague (1986). Besides stimulating cartilage formation, TGF-$\beta$ is synthesized and secreted in bone cell cultures, and stimulates the growth of subconfluent layers of fetal bovine bone cells, thus showing it to be an autocrine (or paracrine) regulator of bone cell development. Sporn & Roberts (1985). Like TGF-$\beta$, the IGFs are found in high concentrations in bone. In fact, IGFs are the most abundant growth factors in bone (Mohan, 1993, and references therein). Both TGF-$\beta$ and the IGF proteins are involved in the coupling of bone reabsorption to bone formation. TGF-$\beta$ is present in bone as a latent complex in bone ECM, and is thought to be activated by the osteoclast's acidic environment. Fawthrop et al. (1992); Bonewald & Mundy (1990). Increased bone reabsorption thus results in an increased release and activation of TGF-$\beta$ which subsequently stimulates osteogenic cells. Likewise, IGFs are found in bone, but are complexed with IGF-binding proteins. Mohan (1993); Feyen et al. (1991). These IGF-binding proteins (IGFBPs) inhibit the biological actions (proliferation and matrix synthesis) of IGF in a dose-dependent manner. Feyen et al. (1991). Within the bone, IGF-binding proteins (in particular, IGFBP-5) bind with high affinity to both hydroxyapatite and IGF. Therefore, bone reabsorption (as with TGF-$\beta$) releases active IGFs that subsequently stimulate osteogenic cells in a paracrine manner. Mohan (1993). While much is known about both the storage of osteogenic growth factors in bone and, in some cases, their production by osteoblasts, little is understood concerning their relative role in bone formation.

As mentioned, IGF-II and TGF-β represent the first and second most abundant mitogens in human bone extracellular matrix (ECM). Importantly, IGFs are dysregulated in postmenopausal osteoporosis (Komori et al., 1997), and are decreased during caloric restriction. Bourrin et al. (2000). IGFs are synthesized by osteoblasts and as such may serve autocrine or paracrine functions. Farley et al. (2000). Moreover, osteoblasts respond to hormonal signals such as increased growth hormone or calcitonin by increasing IGF synthesis. Farley et al. (2000); Conover (1996). On a cellular basis, IGFs function to stimulate osteoblast proliferation (Farley, 2000; Thomas et al., 1999; Zambonin et al., 1999), activating MAP kinases such as ERK-1 and ERK-2 (Chaudhary & Avioli, 1998) and targeting early response genes such as c-myc (Conover Bale, 1998). The roles of IGFs in bone formation are complex, and reports are often contradictory. It is well understood that IGFs function in relation to their binding proteins (IGFBPs). All 6 of the IGFBPs bind IGF with high affinity and, therefore, inhibit IGF function. Interestingly, the IGFBPs show skeletal or site-dependent differences in distribution (Malpe et al., 1997), with human trabecular osteoblasts producing IGFBP3, IGFBP4, and IGFBP5 (Conover, 1996). TGF-β may be part of this regulatory loop as it is known to both stimulate osteoblast development (Sporn & Roberts, 1985) and to inhibit the production of IGFBPs 4 and 5 (Conover, 1996). In contrast, IGFBPs also are reported to augment IGF actions on osteoblast development. Thus, IGFBP3 internalization and processing is reported to markedly enhance IGF receptor signaling, but requires pretreatment with IGFBP3 that, alone, had no effect. Likewise, IGFBP5 stimulates osteoblast proliferation in vitro or in vivo, either alone or in combination with IGF. Richman et al. (1999).

Little information exists on the microenvironmental influences regulating the commitment of bone marrow cells into the bone lineage. One of the obligate requirements for tissue formation is the appropriate queuing of developmental signals within a three-dimensional tissue architecture. For example, the developmentally regulated condensation of embryonic chondrocytes leads to their differentiation and eventual establishment of the skeleton. Consistent with this, the present inventors recently demonstrated that three-dimensional cellular condensation is essential for the ex vivo formation of human bone. A similar process occurs in the early phases of murine long-term bone marrow cultures (LTBMC) where the establishment of hematopoietic foci represents a three dimensional cellular structure. However, the potential of these foci to become osteogenic, and the microenviromental factors regulating such a process are poorly understood.

Figure 10:
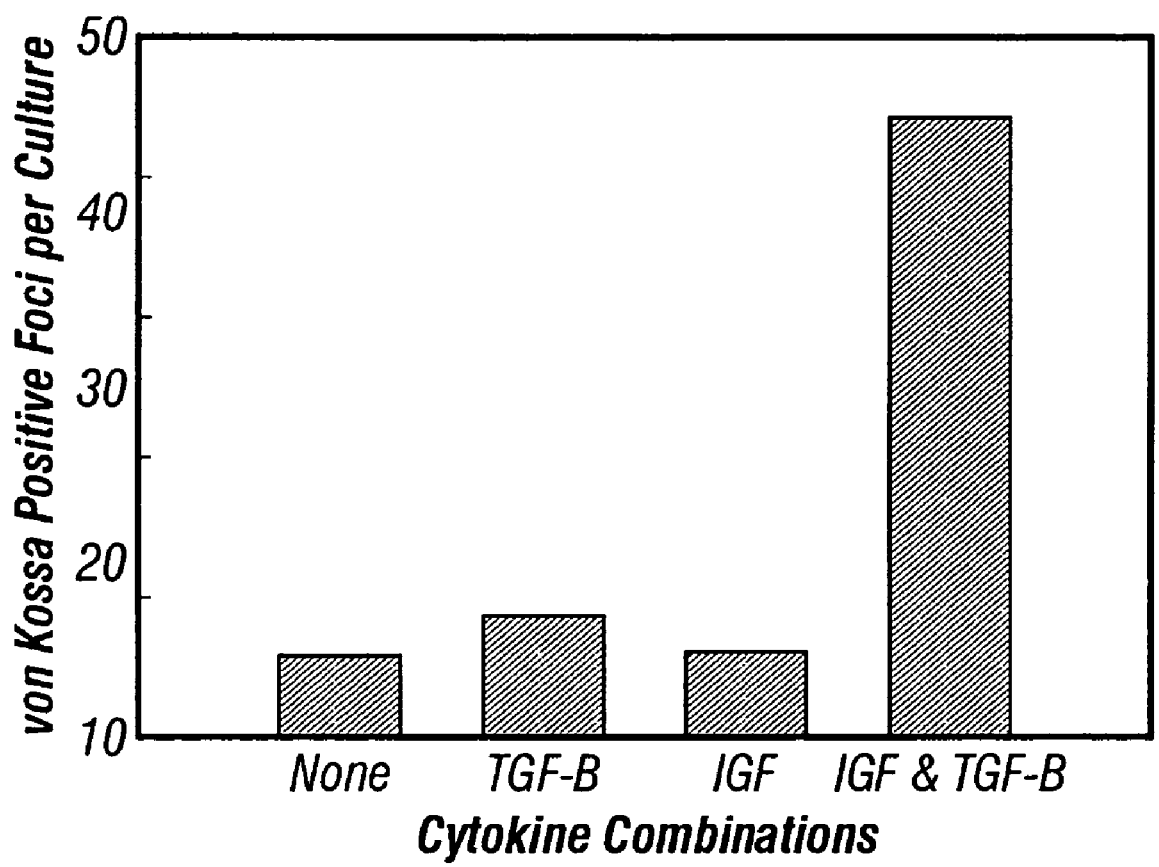
FIG. 10. TGF-β and IGF Act Synergistically During Osteogenesis. Using a murine culture system, von Kossa positive microspicules were quantified in the presence of bone-active cytokines. TGF-β, Transforming Growth Factor β1; IGF, Insulin-Like Growth Factor.

The inventors therefore established murine LTBMC and probed their capacity to express markers of osteogenesis. They have extended these studies of osteogenesis to exploring the microenvironmental control of ex vivo bone formation. Additionally, they have developed a smaller culture volume system (dropping from 100-mm tissue culture dishes to 35 mm ones) to allow better utilization of human osteoblasts. Using this modification on murine cells (which respond less robustly to TGF-β as a solitary cytokine), the inventors examined the role of IGF in modulating this process. Unlike the human culture system, murine osteogenesis was observed using unfractionated bone marrow and serum-containing conditions. These conditions, while different, generate microspicules very similar in nature to those observed in the human system. As serum-free, chemically defined media are a refinement of serum-containing cultures, and human bone marrow also generate osteogenic cells, the murine data can be directly extrapolated to the human Individually, TGF-b (25 pM) and IGF (15 pM) have little capacity to drive murine osteogenesis, whereas together they result in a marked (8-fold) increase in von-Kossa positive Microspicules foci per culture (FIG. 10). It should be noted that only IGF+TGF-β result in microspicule formation; other conditions only generate von Kossa positive mineralization of the matrix, but no evidence of bone formation. Within one week, normal LTBMC (Dexter Cultures) show marked numbers of developmental foci that express two markers of osteogenesis: the presence of collagen (as detected by the Masson staining reaction), and a positive von Kossa staining reaction that detect the presence of calcium phosphate. These cultures also showed the presence of crystalline structures (termed microspicules) consisting of organized, microcrystalline murine bone. Endothelial cells are important sources of cytokines for both hematopoietic and osteogenesis cells. An important regulator of endothelial cells, VEGF, is known to affect both endothelial cells, and bone cell development (although it is not clear if the latter is a direct effect). The addition of VEGF (10 ng/mL) to LTBMC results in a 75-80% increase in the number of collagen-positive and von Kossa-positive developmental foci per culture. Importantly, VEGF also stimulates an increase in the number of microspicules per culture, generating an approximate 5-fold increase in the number of microspicules per culture over the first three weeks of culture. As well, VEGF increases the number of von Kossa cellular foci 2.5-fold, suggesting that VEGF is involved in mineralization. The inventors conclude that murine LTBMC can be established under conditions that promote osteogenesis. The use of these cultures to detail the regulatory influences regulating the commitment of stem cells to the osteogenic lineage will be important to the understanding of the complexities of bone cell development.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allcock & Fuller, "Synthesis and Hydrolysis of Hexakis (imidazolyl)cyclotriphosphazene, "*J. Am. Chem. Soc.,* 103, 2250-2256, 1981.

Aubin et al., *J. of Cell Biol.* 92:452-461, 1982.

Baichwal and Sugden, *In: Gene Transfer*, Kucherlapati R, ed., New York, Plenum Press, pp. 117-148, 1986.

Barnard et al., *Biochim. Biophys. Acta.* 1032:79-87, 1990.

Barnes and Sam, "Serum-free cell culture: A unifying approach," *Cell* 22: 649-655, 1980.

Barnes, "Serum-free animal cell culture," *Bio Techniques* 5: 534-542, 1987.

Benvenisty and Neshif, *Proc. Nat'l Acad. Sci. USA*, 83:9551-9555, 1986.

Bonadio and Goldstein, "Our understanding of inherited skeletal fragility and what this has taught us about bone structure and function," in Molecular and Cellular Biology of Bone, Noda, M., ed., Academic Press, Inc., San Diego, Calif. pp. 169-189, 1993.

Bonewald & Mundy, "Role of transforming growth factor-beta in bone remodeling." *Clin Orthop* 250:261-276, 1990.

Bourrin et al., "Dietary protein restriction lowers plasma insulin-like growth factor I (IGF-I), impairs cortical bone formation, and induces osteoblastic resistance to IGF-I in adult female rats." *Endocrin* 141:3149-3155, 2000.

Broad, Boraston, and Rhodes, "Production of recombinant proteins in serum-free media," *Cytotechnology* 5: 47-55, 1991.

Bruder and Caplan, *Bone*, 10:359-375, 1989.

Bruder and Caplan, *Bone*, 11:189-198, 1990.

Bruder et al., *Trans. Ortho. Res. Soc.*, 16:58, 1991.

Bruland et al., *Cancer Res*, 48:5302-5308, 1988.

Byers and Steiner, "Osteogenesis imperfecta," *Annu. Rev. Med.* 43:269-289, 1992.

Carter and Flotte, *Gene Ther.* 2(6):357-62 1995.

Centrella, "Transforming growth factor β is a bifunctional regulator of replication and collagen synthesis in osteoblast-enriched cell cultures from fetal rat bone," *J Biol Chem* 262:2869-2874, 1987.

Chatterjee, et al., *Ann. N.Y. Acad. Sci.*, 770:79-90, 1995.

Chaudhary & Avioli, "Identification and activation of mitogen-activated protein (MAP) kinase in normal human osteoblastic and bone marrow stromal cells: attenuation of MAP kinase activation by cAMP, parathyroid hormone and forskolin." *Mol Cell Biochem* 178:59-68, 1998.

Cheifetz et al., *Cell* 48, 409-415, 1987.

Chen and Okayama, *Mol Cell Biol.*, 7:2745-2752, 1987.

Chen et al., *Exp. Cell Res.*, 195:509, 1991.

Chen et al., *Exp. Cell Res.*, 206:199, 1993.

Chen, Weinberg, *Proc. Nat'l Acad. Sci. USA*, 92:1565-1569, 1995.

Cheng et al., *Endocrinology*, 134:277, 1994.

Coffin, In: *Virology*, ed., New York: Raven Press, pp. 1437-1500, 1990.

Conover, C A, "The role of Insulin-like growth factors and binding proteins in bone cell biology," in Rodan G A, Raisz L G, Rodan G A (eds): Principles of Bone Biology, New York, Academic Press, 1996, p 607-626.

Conover & Bale, "Insulin-like growth factor I induction of c-myc expression in bovine fibroblasts can be blocked by antecedent insulin receptor activation." *Exp Cell Res* 238:122-127, 1998.

Costantino et al., *Arch. Otolaryngol. Head Neck Surg.* 117(4), 379-384, 1991.

Coupar et al., *Gene*, 68:1-10, 1988.

"Cynamid Research Develops World's First Synthetic Absorbable Suture," Chemistry and Industry, 905 (1970).

De Martin et al., *EMBO J.* 6, 3673-3677, 1987.

Denker, "Formation of cartilage-like spheroids by micromass cultures of murine C3H10T1/2 cells upon treatment with transforming growth factor-β1," *Differentiation* 59:25-34, 1995.

Denker, Nicoll, Tuan, "Formation of cartilage-like spheroids by micromass cultures of murine C3H10T1/2 cells upon treatment with transforming growth factor-beta 1," *Differentiation* 59:25-34, 1995.

Derynck et al., *J. Biol. Chem.* 261, 4377-4379, 1986.

Derynck et al., *Nature* 316,701-705, 1985.

Doctor et al., *Dev. Biol.* 151:591-505, 1992

Dubensky et al., *Proc. Nat'l Acad. Sci. USA*, 81:7529-7533, 1984.

Dunlop, Hall, "Relationships between cellular condensation, preosteoblast formation and epithelial-mesenchymal interactions in initiation of osteogenesis," *International Journal of Developmental Biology* 39:357-371, 1995.

Elgendy et al., "Osteoblast-like cell (MC3T3-E1) proliferation on bioerodible polymers: An approach towards the development of a bone-bioerodible polymer composite material," *Biomaterials*, 14, 263-269, 1993.

Elias, in Principles and Techniques in diagnostic histopathology, Park Ridge, N.J., Noyes Publication, 248-250, 1982.

Embleton et al., *Br J Cancer*, 43:582-587, 1981.

EP 128 733

EP 273 085

EP 481 791

Farley et al., "Calcitonin increases the concentration of insulin-like growth factors in serum-free cultures of human osteoblast-line cells." *Calc Tiss Res* 67:247-254, 2000.

Fawthrop et al., "The effect of transforming growth factor beta on the plasminogen activator activity of normal human osteoblast-like cells and a human osteosarcoma cell line MG-63." *J Bone Miner Res* 7:1363-1371, 1992.

Fechheimer et al., *Proc. Nat'l Acad. Sci. USA*, 84:8463-8467, 1987.

Ferkol et al., *FASEB J.*, 7:1081-1091, 1993.

Ferrari et al., *J. Virol*, 70:3227-3234, 1996.

Feyen et al., "Recombinant human [Cys281]insulin-like growth factor-binding protein 2 inhibits both basal and insulin-like growth factor I-stimulated proliferation and collagen synthesis in fetal rat calvariae." *J Biol Chem* 266:19469-19474, 1991.

Fisher et al., *J. Virol.*, 70:520-532, 1996.

Flotte et al., *Proc. Nat'l Acad. Sci. USA*, 90:10613-10617, 1993.

Fraley et al., *Proc. Nat'l Acad. Sci USA*, 76:3348-3352, 1979.

Frame, *Int J Oral Maxillofac Surg.* 16(6):642-55, 1987.

Franceschi, "1α,25-Dihydroxyvitamin D3 specific regulation of growth, morphology, and Fibronectin in a human osteosarcoma cell line," *J Cell Physiol* 123:401-409, 1985.

Franceschi, "Regulation of Type I Collagen Synthesis by 1,25-Dihydroxyvitamin D3 in Human Osteosarcoma cells," *J Biol Chem* 263:18938-18945, 1988.

Friedman et al., *Arch. Otolaryngol. Head Neck Surg.* 117(4), 386-389, 1991.

Gasmi, Glynn, Jin, Jolly, Yee, Chen, "Requirements for efficient production and transduction of human immunodeficiency virus type 1-based vectors," *J Virol* 73(3): 1828-34, 1999.

Gerhart et al., *Trans Orthop Res Soc*, 16:172, 1991.

Ghosh and Bachhawat, In: Liver diseases, targeted diagnosis and therapy using specific receptors and ligands, (Wu G, Wu C ed.), New York: Marcel Dekker, pp. 87-104, 1991.

Glowacki et al., *Clin. Plast. Surg.* 12(2), 233-241, 1985.

Gomori, "A rapid one-step trichrome stain," *Am J Clin Pathol* 20:661, 1950.

Goodman et al., *Blood*, 84:1492-1500, 1994.

Gopal, *Mol. Cell Biol.*, 5:1188-1190, 1985.

Graham and Van Der Eb, *Virology*, 52:456467, 1973.

Hall, Miyake, "Divide, accumulate, differentiate: cell condensation in skeletal development revisited," *International Journal of Developmental Biology* 39:881-893, 1995.

Hall, Miyake, "The membranous skeleton: the role of cell condensations in vertebrate skeletogenesis," *Anatomy & Embryology* 186:107-124, 1992.

Harada, *Shikwa-Gakuho* 89(2), 263-297, 1989.

Harlow & Lane, *Antibodies "A Laboratory Manual*, Cold Spring Harbor Laboratory, 1988.

Hay et al., *J. Mol. Biol.,* 175:493-510, 1984.

Hayat in Principles and Techniques of Electron Microscopy. Biological Applications., Boca Raton, Fla., CRC Press, Inc., 1989.

Hearing and Shenk, *J. Mol. Biol.* 167:809-822, 1983.

Hearing et al., *J. Virol.,* 67:2555-2558, 1987.

Heiner et al., *Cancer Res,* 47:5377-5384, 1987.

Hollinger and Battistone, "Biodegradable Bone Repair Materials," *Clinical Orthopedics and Related Research,* 207, 290-305, 1986.

Hosoi et al., *Cancer Res,* 42:654-661, 1982.

Ignotz & Massague, "Transforming growth factor-beta stimulates the expression of fibronectin and collagen and their incorporation into the extracellular matrix." *J Biol Chem* 261:4337-4345, 1986.

Jayme, D. *Cytotechnology* 5(1):15-30, 1991.

Kaneda et al., *Science,* 243:375-378, 1989.

Kaplitt et al., *Nat. Genet.,* 8:148-153, 1994.

Kato et al, *J. Biol. Chem.,* 266:3361-3364, 1991.

Kessler et al., *Proc. Nat'l Acad. Sci. USA,* 93:14082-14087, 1996.

Kim, Rey, Glimcher, "X-ray diffraction, electron microscopy, and Fourier transform infrared spectroscopy of apatite crystals isolated from chicken and bovine calcified cartilage," *Calcif Tissue Int* 59:58-63, 1996.

Kimura et al., *Biomed. Res.,* 5:465, 1984.

Kim et al., *Nature* 362:841-844, 1993.

Klein et al., *Nature,* 327:70-73, 1987.

Koeberl et al., *Proc. Nat'l Acad. Sci. USA,* 94:1426-1431, 1997.

Kojima et al., *J. Cell Biol.* 113(6):1439-1445, 1991.

Komori et al., "Fargeted disruption of Cbfa1 results in a complete lack of bone formation owing to maturational arrest of osteoblasts [see comments]." *Cell* 89:755-764, 1997.

Kulkarni et al., *J. Biomedical Materials Research,* 5, 169-81, 1971.

Langille et al., *Differentiation,* 40:84, 1989.

Laurencin et al., "Use of polyphosphazenes for skeletal tissue regeneration," *J. Biom. Mater. Res.,* 27, 1993.

Lawson et al., *Clin Chem,* 31:381-385, 1985.

Levrero et al., *Gene,* 101: 195-202, 1991.

Lillie, "Further experiments with Massons trichrome modification of Mallory's connective tissue stain," *Stain Technol* 15:17, 1940.

Long, "Expression of human bone-related proteins in the hematopoietic microenvironment," *J Clin Invest* 86:1387-1395, 1990.

Long, "Regulation of human bone marrow-derived osteoprogenitor cells by osteogenic growth factors," *J Clin Invest* 95:881-887, 1995.

Malpe et al., "Insulin-like growth factor (IGF)-I, -II, IGF binding proteins (IGFBP)-3, -4, and -5 levels in the conditioned media of normal human bone cells are skeletal site-dependent.: *J Bone Min Res* 12:423-430, 1997.

Mann et al., *Cell,* 33:153-159, 1983.

Marden et al., *J. Craniofac. Surg.* 1(3), 154-160, 1990.

Marquardt et al., *J. Biol. Chem.* 262,12127-12131, 1987.

Massague, J, "The TGF-beta family of growth and differentiation factors." *Cell* 49:437-438, 1987.

Massague et al., *Trends Cell Biol.* 4:172-178, 1994.

McCown et al., *Brain Res.,* 713:99-107, 1996.

McGee, Russell, "Histochemical methods for calcium," *J Histochem* 6:22-42, 1958.

Mendelsohn, "FT-IR microscopy of endochondral ossification at 20 u spatial resolution," *Calcif Tissue Int* 44:20-24, 1989.

Miyake, Cameron, Hall, "Stage-specific onset of condensation and matrix deposition for Meckel's and other first arch cartilages in inbred C57BL/6 mice," *Journal of Craniofacial Genetics & Developmental Biology* 16:3247, 1996.

Miyazono et al., *Adv. Immunol.* 55:181-220, 1994.

Mizukami et al., *Virology,* 217:124-130, 1996.

Mohan, S: Insulin-like growth factor binding proteins in bone cell regulation. *Growth Regulation* 3:67-70, 1993.

Nicolas and Rubenstein, In: *Vectors: A survey of molecular cloning vectors and their uses*, Rodriguez and Denhardt (eds.), Stoneham: Butterworth, pp. 493-513, 1988.

Nicolau and Sene, *Biochim. Biophys. Acta,* 721:185-190, 1982.

Nicolau et al, *Methods Enzymol.,* 149:157-176, 1987.

Nikol et al, *J. Clin. Invest.* 90:1582-1592, 1992.

Oberlender, Tuan, "Spatiotemporal profile of N-cadherin expression in the developing limb mesenchyme," *Cell Adhesion & Communication* 2:521-537, 1994.

Ohgushi et al, *Acta Orthop. Scand.* 60(3), 334-339, 1989.

Ono et al, *Biomaterials* 11(4), 265-271, 1990.

Padgett et al, *Nature (London),* 325:81-84, 1987.

Parsons et al., *Ann NY Acad Sci.* 523:190-207, 1988.

Paschalis, Jacenko, Olsen, Mendelsohn, Boskey, "Fourier transform infrared microspectroscopic analysis identifies alterations in mineral properties in bones from mice transgenic for type X collagen," *Bone* 19:151-156, 1996.

Paskind et al, *Virology,* 67:242-248, 1975.

Passuti et al, *Clin. Orthop.* 248, 169-176, 1989.

Perales et al, *Proc. Nat'l Acad. Sci. USA* 91:4086-4090, 1994.

Ping et al, *Microcirculation,* 3:225-228, 1996.

Pinholt et al, *J. Oral Maxillofac. Surg.* 50(8), 859-867, 1992.

Pinholt et al, *Scand. J. Dent. Res.* 99(2), 154-161, 1991.

Plate et al, *Nature* 359:845-848, 1992.

Pochon et al, *Z-Kinderchir.* 41(3), 171-173, 1986.

Potter et al, *Proc. Nat'l Acad. Sci. USA,* 81:7161-7165, 1984.

Prockop, "Mutations that alter the primary structure of type I collagen. The perils of a system for generating large structures by the principle of nucleated growth," *J. Biol. Chem.* 265:15349-15352, 1990.

Radler et al, *Science,* 275:810-814, 1997.

Renan, *Radiother. Oncol.,* 19:197-218, 1990.

Rey, "Characterization of the apatite crystals of bone and their maturation in osteoblast cell culture: Comparison with native bone crystals," *Connective Tiss Res* 35:397-403, 1996.

Rey, "Structural and chemical characteristics and maturation of the calcium-phosphate crystals formed during the calcification of the organic matrix synthesized by chicken osteoblasts in cell culture," *J Bone Miner Res* 10:1577-1588, 1995.

Richman et al., "Recombinant human insulin-like growth factor-binding protein-5 stimulates bone formation parameters in vitro and in vivo." *Endocrin* 140:4699-4705, 1999.

Ridgeway, In: Vectors: A survey of molecular cloning vectors and their uses, Rodriguez R L, Denhardt D T, ed., Stoneham:Butterworth, pp. 467-492, 1988.
Rinderknecht, J. Biol. Chem. 253:2769 (1978a).
Rinderknecht, FEBS Lett 89:283 (1978b).
Rippe et al., Mol. Cell Biol., 10:689-695, 1990.
Roberts and Sporn, eds. The Transforming Growth Factor-βs in Peptide Growth Factors and Their Receptors. I. Handbook of Experimental Pharmacology, vol. 95/I (Springer-Verlag, Berlin,) 419-472, 1990.
Robey and Termine, "Human bone cells in vitro," Calcif Tissue Int 37:453-460, 1985.
Roesgen, Unfallchirurgle 16(5), 258-265, 1990.
Roux et al., Proc. Nat'l Acad. Sci. USA, 86:9079-9083, 1989.
Sambrook et al., In: Molecular Cloning: A Laboratory Manual, 2d Ed., Cold Spring Harbor Laboratory Press, Cold Spring Harbor, N.Y., 1989.
Samulski et al., J. Virol., 61(10):3096-3101, 1987.
Sanger et al., Cancer 46:5629-5632, 1986.
Schweiki et al., Nature 359:843-845, 1992.
Sharples et al., DNA 6, 239-244, 1987.
Shull, Tracy, and Mann, "Identification of a vitamin D responsive protein on the surface of human osteosarcoma cells," Proc. Nat'l Acad. Sci. USA 86:5405-5410, 1989.
Smith, "Measurement of protein using bicinchoninic acid," Anal Biochem 150:76-85, 1985.
Sporn et al., Science, 233:532-534, 1986.
Sporn & Roberts, "Autocrine growth factors and cancer." Nature 313:745-747, 1985.
Stringa, Love, McBride, Suyama, Tuan, "In vitro characterization of chondrogenic cells isolated from chick embryonic muscle using peanut agglutinin affinity chromatography," Exp Cell Res 232:287-294, 1997.
Syftestad et al., Differentiation, 29:230, 1985.
Sykes, "The estimation of two collagens from human dermis by interrupted gel electrophoresis," Biochem Biophys Res Commun 72:1472-1480, 1976.
Temin, In: Gene Transfer, Kucherlapati (ed.), New York: Plenum Press, pp. 149-188, 1986.
Ten Dijke et al., Proc. Nat'l Acad. Sci USA 85, 4715-4719, 1988.
Tenenbaum et al., Calcif. Tissue Int., 34:76, 1982.
Thomas et al., "Response of bipotential human marrow stromal cells to insulin-like growth factors: effect on binding protein production, proliferation, and commitment to osteoblasts and adipocytes." Endocrinology 140: 5036-5044, 1999.
Tibbetts Cell, 12:243-249, 1977.
Toriumi et al., Arch. Otolaryngol Head Neck Surg., 117: 1101-1112, 1991.
Towbin, "Electrophoretic transfer of proteins from polyacrylamide gels to nitrocellulose sheets: procedure and some applications," Proc Nat'l Acad Sci USA 76:4350-4354, 1979.
Tsai et al., Cancer Res, 50:152-161, 1990.
Tur-Kaspa et al., Mol. Cell Biol., 6:716-718, 1986.
Turksen et al., J Histochem Cytochem, 40:1339-1352, 1992.
U.S. Pat. No. 1,995,970
U.S. Pat. No. 2,676,945
U.S. Pat. No. 2,683,136
U.S. Pat. No. 2,703,316
U.S. Pat. No. 2,758,987
U.S. Pat. No. 2,951,828
U.S. Pat. No. 3,531,561
U.S. Pat. No. 4,352,883
U.S. Pat. No. 4,443,546
U.S. Pat. No. 4,533,637
U.S. Pat. No. 5,013,649
U.S. Pat. No. 5,643,736
U.S. Pat. No. 5,972,703
Vukicevic et al., Proc. Nat'l Acad. Sci. USA, 86:8793, 1989.
Wade et al., "Biocompatibility of eight poly(organophosphazenes)," in Organomet. Polym., C. E. Carraher, J. E. Sheats and C. U. Pitman, Jr., Eds., Academic Press, New York, pp. 283-288, 1978.
Wagner et al., Proc. Nat'l Acad. Sci. USA 87(9):3410-3414, 1990.
Walsh et al., J Bone Miner Res, 9:1687-1696, 1994.
Watt et al., Proc. Nat'l Acad. Sci. USA, 83(2): 3166-3170, 1986.
Weeks and Melton, Cell, 51:861-867, 1987.
White et al. "Lentivirus vectors using human and simian immunodeficiency virus elements," J Virol. 73(4):2832-40, 1999.
WO 93/98826
WO 95/06112
Wong et al., Gene, 10:87-94, 1980.
Wong, Tuan, "Interactive cellular modulation of chondrogenic differentiation in vitro by subpopulations of chick embryonic calvarial cells," Developmental Biology (Orlando) 167:130-147, 1995.
Woodward, Tuan, "N-Cadherin expression and signaling in limb mesenchymal chondrogenesis: stimulation by poly-L-lysine," Developmental Genetics 24:178-187, 1999.
Wozney, "Bone Morphogenetic Proteins and Their Gene Expression," in Cellular and Molecular Biology of Bone, (Academic Press, Inc.) pp. 131-167, 1993.
Wrana et al, Nature 370:341-347, 1994.
Wu and Wu, Adv. Drug Delivery Rev., 12:159-167, 1993.
Wu and Wu, Biochem., 27:887-892, 1988.
Wu and Wu, J. Biol. Chem., 262:4429-4432, 1987.
Xiao et al., J. Virol., 70:8098-8108, 1996.
Yang et al., Proc. Nat'l Acad. Sci USA, 87:9568-9572, 1990.
Zambonin et al., "Hydroxyapatite coated with insulin-like growth factor 1 (IGF1) stimulates human osteoblast activity in vitro." Acta Orthop Scand 70:217-220, 1999.

What is claimed is:

1. A method for identifying a modulator of bone formation comprising the steps of:
   a) obtaining an osteogenic cell or bone precursor cell;
   b) culturing said cell under serum-free conditions in the presence of a candidate compound, in the absence of osteogenic growth factors;
   c) measuring bone cell spheroid formation; and
   d) comparing the formation of bone cell spheroid with that observed in the absence of the candidate compound;
   wherein an increase or decrease in bone cell spheroid formation indicates the candidate compound is a modulator of bone cell spheroid formation.

2. The method of claim 1, further comprising the steps of:
   e) obtaining an osteogenic cell or bone precursor cell;
   f) culturing said cell under serum-free conditions in the presence of growth factors of the TGF-β gene superfamily;
   g) maintaining the cell culture at cell densities that allows the formation of a bone cell spheroid;
   h) measuring bone cell spheroid formation; and
   i) comparing the bone spheroid formation measured in step c) to the bone spheroid formation measured in step h).

3. The method of claim 2, wherein the culture conditions of step f) are free of the candidate compound.

4. The method of claim 2, wherein the culture conditions of step f) further comprise the candidate compound.

5. A method for producing a modulator of bone formation, comprising the steps of:
   a) obtaining an osteogenic cell or bone precursor cell;
   b) culturing said cell under serum-free conditions in the presence of a candidate compound, in the absence of osteogenic growth factors;
   c) measuring bone cell spheroid formation; and
   d) comparing the formation of bone cell spheroid with that observed in the absence of the candidate compound, wherein an increase or decrease in bone cell spheroid formation indicates the candidate compound is a modulator of bone cell spheroid formation;
   e) identifying the candidate compound as a modulator of bone cell formation; and
   f) producing the modulator so identified.

* * * * *